(12) United States Patent
Ozerov et al.

(10) Patent No.: US 12,357,151 B2
(45) Date of Patent: **\*Jul. 15, 2025**

(54) ANALYSIS AND VISUALIZATION OF DENTAL ARCH OVER TIME

(71) Applicant: Align Technology, Inc., San Jose, CA (US)

(72) Inventors: Sergei Ozerov, Moscow (RU); Ofer Saphier, Rechovot (IL); Avi Kopelman, Palo Alto, CA (US); Adi Levin, Nes Tziona (IL); Pavel Razumovskiy, Tambov (RU); Michael Sabina, Campbell, CA (US); Mikhail Dyachenko, Moscow (RU); Rene M. Sterental, Palo Alto, CA (US); Partha Dey, San Jose, CA (US); Roman A. Roschin, Moscow (RU); Anton Gavrilov, Moscow (RU); Leonid Vyacheslavovich Grechishnikov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 17/864,320

(22) Filed: Jul. 13, 2022

(65) Prior Publication Data
US 2022/0346629 A1 Nov. 3, 2022

Related U.S. Application Data

(63) Continuation of application No. 16/583,091, filed on Sep. 25, 2019, now Pat. No. 11,426,053, which is a
(Continued)

(51) Int. Cl.
*A61C 7/00* (2006.01)
*A61B 1/00* (2006.01)
(Continued)

(52) U.S. Cl.
CPC .... *A61B 1/000094* (2022.02); *A61B 1/00009* (2013.01); *A61B 1/00016* (2013.01);
(Continued)

(58) Field of Classification Search
CPC .......... A61B 1/000094; A61B 1/00009; A61B 5/0088; A61B 5/1111; A61B 5/4547;
(Continued)

(56) References Cited

U.S. PATENT DOCUMENTS 6,099,314 A 8/2000 Kopelman et al.
6,334,772 B1 1/2002 Taub et al.
(Continued)

OTHER PUBLICATIONS

Co-pending U.S. Appl. No. 16/784,493, inventor Babayoff; Noam, filed Feb. 7, 2020.
(Continued)

*Primary Examiner* — Kent Yip
(74) *Attorney, Agent, or Firm* — Lowenstein Sandler LLP

(57) ABSTRACT

A processing device may execute instructions from a computer readable medium to perform operations comprising: making a comparison between first image data of at least a portion of a dental arch and second image data of at least the portion of the dental arch; determining a plurality of differences between a first representation of at least the portion of the dental arch in the first image data and a second representation of at least the portion of the dental arch in the second image data; determining that a first difference of the plurality of differences is attributable to tooth movement; determining that a second difference of the plurality of differences is attributable to tooth wear to one or more teeth on at least a portion of the dental arch; and generating a third representation of at least the portion of the dental arch that
(Continued)

is a modified version of the second representation, wherein a visual indication of the tooth wear is provided in the third representation.

28 Claims, 22 Drawing Sheets

Related U.S. Application Data continuation of application No. 15/858,940, filed on Dec. 29, 2017, now Pat. No. 10,499,793.

(60) Provisional application No. 62/492,047, filed on Apr. 28, 2017, provisional application No. 62/460,707, filed on Feb. 17, 2017.

(51) Int. Cl.
| | |
|---|---|
| *A61B 1/04* | (2006.01) |
| *A61B 1/24* | (2006.01) |
| *A61B 5/00* | (2006.01) |
| *A61B 5/11* | (2006.01) |
| *A61B 6/00* | (2006.01) |
| *A61B 6/51* | (2024.01) |
| *G16H 30/40* | (2018.01) |
| *G16H 50/50* | (2018.01) |
| *A61B 1/06* | (2006.01) |

(52) U.S. Cl.
CPC ........ *A61B 1/0002* (2013.01); *A61B 1/00194* (2022.02); *A61B 1/04* (2013.01); *A61B 1/24* (2013.01); *A61B 5/0088* (2013.01); *A61B 5/1111* (2013.01); *A61B 5/4547* (2013.01); *A61B 5/4552* (2013.01); *A61B 5/7221* (2013.01); *A61B 5/725* (2013.01); *A61B 5/7264* (2013.01); *A61B 6/51* (2024.01); *A61B 6/5247* (2013.01); *A61C 7/002* (2013.01); *G16H 30/40* (2018.01); *G16H 50/50* (2018.01); *A61B 1/043* (2013.01); *A61B 1/0638* (2013.01); *A61B 2560/0276* (2013.01)

(58) Field of Classification Search
CPC ....... A61B 5/4552; A61B 5/7221; A61B 6/51; A61B 6/5247; A61C 7/002; G16H 30/40; G16H 50/50
See application file for complete search history.

(56) References Cited

U.S. PATENT DOCUMENTS

| | | | |
|---|---|---|---|
| 6,334,853 B1 | 1/2002 | Kopelman et al. | |
| 6,463,344 B1 | 10/2002 | Pavlovskaia et al. | |
| 6,542,249 B1 | 4/2003 | Kofman et al. | |
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,610,106 B2 | 4/2020 | Kopelman et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,792,127 B2 * | 10/2020 | Kopelman | A61C 7/002 |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 11,096,765 B2 | 8/2021 | Atiya et al. | |
| 11,238,586 B2 | 2/2022 | Minchenkov et al. | |
| 11,367,192 B2 | 6/2022 | Kopelman et al. | |
| 2008/0318179 A1 * | 12/2008 | Liu | A61C 7/00 433/24 |
| 2016/0220200 A1 | 8/2016 | Sandholm et al. | |
| 2019/0029784 A1 | 1/2019 | Moalem et al. | |
| 2019/0060042 A1 | 2/2019 | Fisker et al. | |
| 2019/0388193 A1 | 12/2019 | Saphier et al. | |
| 2020/0281702 A1 | 9/2020 | Kopelman et al. | |
| 2020/0315434 A1 | 10/2020 | Kopelman et al. | |
| 2020/0349705 A1 | 11/2020 | Minchenkov et al. | |
| 2020/0404243 A1 | 12/2020 | Saphier et al. | |
| 2021/0030503 A1 | 2/2021 | Shalev et al. | |
| 2021/0059796 A1 | 3/2021 | Weiss et al. | |
| 2021/0068773 A1 | 3/2021 | Moshe et al. | |
| 2021/0113089 A1 | 4/2021 | Kopelman et al. | |
| 2021/0121049 A1 | 4/2021 | Rudnitsky et al. | |
| 2021/0128281 A1 | 5/2021 | Peleg | |
| 2021/0137653 A1 | 5/2021 | Saphier et al. | |
| 2021/0196152 A1 | 7/2021 | Saphier et al. | |

OTHER PUBLICATIONS

Co-pending U.S. Appl. No. 16/784,501, inventor Noam; Babayoff, filed Feb. 7, 2020.

Co-pending U.S. Appl. No. 16/784,515, inventor Noam; Babayoff, filed Feb. 7, 2020.

Co-pending U.S. Appl. No. 17/032,366, inventor Kopelman; Avi, filed Sep. 25, 2020.

Co-pending U.S. Appl. No. 29/768,525, inventors Zakhar; Ginzburg et al., filed Jan. 29, 2021.

(56) References Cited

OTHER PUBLICATIONS

Co-pending U.S. Appl. No. 29/768,563, inventors Zakhar; Ginzburg et al., filed Jan. 29, 2021.

* cited by examiner

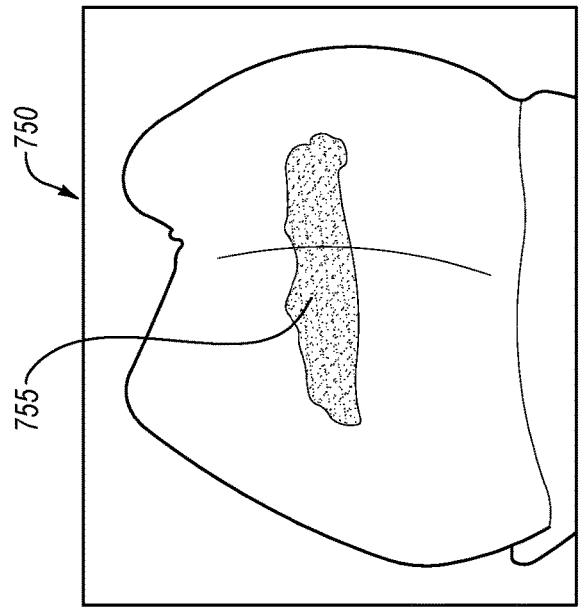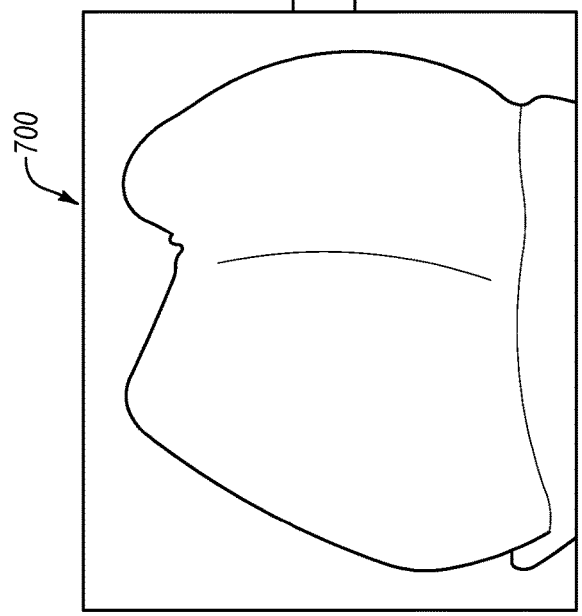
*FIG. 7A*
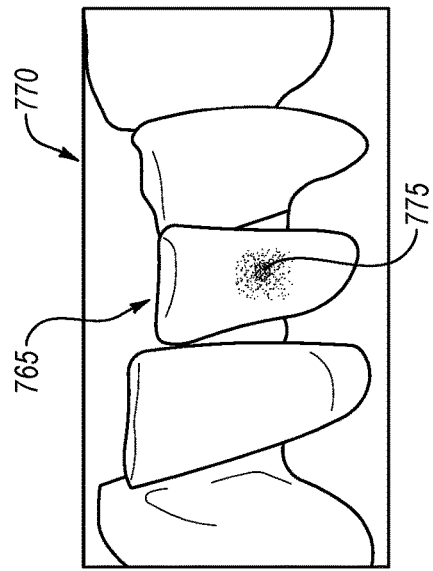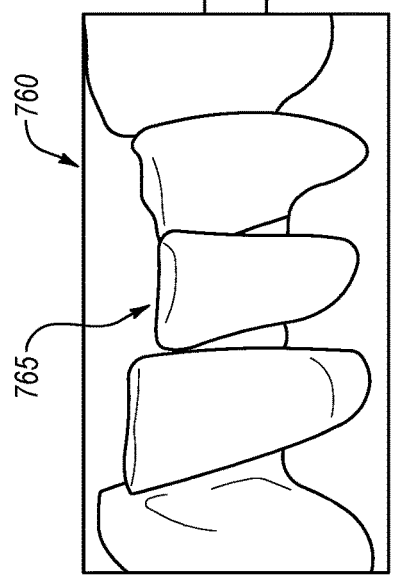
*FIG. 7B*

| Tooth ID | Bucco Lingual Translation, mm | | Mesio-Distal Translation, mm | | Intrusion / Extrusion, mm | | Angulation, Degrees | | Inclination, Degrees | | Rotation, Degrees | | Alert |
|---|---|---|---|---|---|---|---|---|---|---|---|---|---|
| | achieved | planned | achieved | planned | achieved | planned | achieved | planned | achieved | planned | achieved | planned | |
| 2 | 0.0 | 0.0 | 0.0 | 0.0 | 0.0 | 0.0 | 0.0 | 0.0 | 0.0 | 0.0 | 0.0 | 0.0 | Small Movement |
| 3 | 0.0 | 0.0 | 0.0 | 0.0 | 0.0 | 0.0 | 0.0 | 0.0 | 0.0 | 0.0 | 0.0 | 0.0 | Small Movement |
| 4 | 0.0 | 0.1 Ling | 0.0 | 0.0 | 0.0 | 0.0 | 0.0 | 0.0 | 0.0 | 0.7 Dis | 0.0 | 0.8 Lin | Small Movement |
| 5 | 0.0 | 0.1 Buc | 0.0 | 0.0 | 0.0 | 0.1 Ext | 0.0 | 0.4 Dis | 0.0 | 0.7 Dis | 0.0 | 0.7 Lin | Small Movement |
| 6 | 0.0 | 0.1 Buc | 0.0 | 0.1 Dist | 0.0 | 0.0 | 0.1 Dis | 0.3 Dis | 0.0 | 0.1 Mes | 0.0 | 5.2 Lin | |
| 7 | 0.0 | 0.1 Ling | 0.0 | 0.1 Dist | 0.0 | 0.0 | 0.1 Dis | 0.1 Dis | 0.0 | 0.7 Dis | 0.0 | 4.2 Buc | |
| 8 | 0.0 | 0.1 Ling | 0.0 | 0.0 | 0.0 | 0.0 | 0.1 Dis | 0.3 Mes | 0.0 | 0.7 Dis | 0.0 | 4.9 Buc | |
| 9 | 0.0 | 0.1 Ling | 0.0 | 0.0 | 0.0 | 0.1 Ext | 0.0 | 0.6 Mes | 0.0 | 0.1 Dis | 0.0 | 2.5 Buc | |
| 10 | 0.0 | 0.1 Ling | 0.0 | 0.0 | 0.0 | 0.1 Ext | 0.1 Dis | 0.0 | 0.0 | 0.4 Dis | 0.0 | 0.4 Buc | Small Movement |
| 11 | 0.0 | 0.1 Buc | 0.0 | 0.0 | 0.0 | 0.1 Ext | 0.0 | 0.1 Dis | 0.0 | 0.7 Mes | 0.0 | 5.9 Lin | |
| 12 | 0.0 | 0.1 Buc | 0.0 | 0.0 | 0.0 | 0.0 | 0.0 | 0.0 | 0.0 | 0.5 Mes | 0.0 | 0.0 | Small Movement |

FIG. 12

ANALYSIS AND VISUALIZATION OF DENTAL ARCH OVER TIME

RELATED APPLICATIONS

This patent application is a continuation application of U.S. patent application Ser. No. 16/583,091, filed Sep. 25, 2019, which is a continuation application of U.S. patent application Ser. No. 15/858,940, filed Dec. 29, 2017, which claims the benefit under 35 U.S.C. § 119(e) of U.S. Provisional Application No. 62/460,707, filed Feb. 17, 2017, and further claims the benefit under 35 U.S.C. § 119(e) of U.S. Provisional Application No. 62/492,047, filed Apr. 28, 2017, all of which are incorporated by reference herein.

TECHNICAL FIELD

Embodiments of the present invention relate to the field of dentistry and, in particular, to a system and method for performing longitudinal analysis and visualization of an oral cavity (e.g., a dental arch in an oral cavity) under a limited accuracy system.

BACKGROUND

Dental practitioners generally make assessments of clinical problems in a patient's oral cavity based on visual inspection and personal knowledge. However, small changes to tooth and/or gum surfaces can have clinical importance, and it can be difficult for the dental practitioner to identify such small changes. Additionally, the magnitude and rate of change to a patient's dentition may not be easily determined. For example, the dental practitioner may have difficulty in determining the specific, subtle changes that might have occurred to the patient's dentition.

Intraoral scanners are a useful tool in dentistry and orthodontics. However, intraoral scans are not generally used for longitudinal analysis. One reason is that the results of intraoral scans performed by intraoral scanners include errors introduced by the intraoral scanners, which makes comparison between images difficult and error prone.

BRIEF DESCRIPTION OF THE DRAWINGS

Embodiments of the present invention are illustrated by way of example, and not by way of limitation, in the figures of the accompanying drawings.

FIG. 7A illustrates a tooth before and after a change in appearance of the tooth.

FIG. 7B illustrates a set of teeth before and after a change in appearance of one of the teeth.

FIG. 12 illustrates a table showing which teeth have positions that are in compliance with an orthodontic treatment plan and which teeth have positions that deviate from the orthodontic treatment plan, in accordance with an embodiment.

DETAILED DESCRIPTION

Figure 1A:
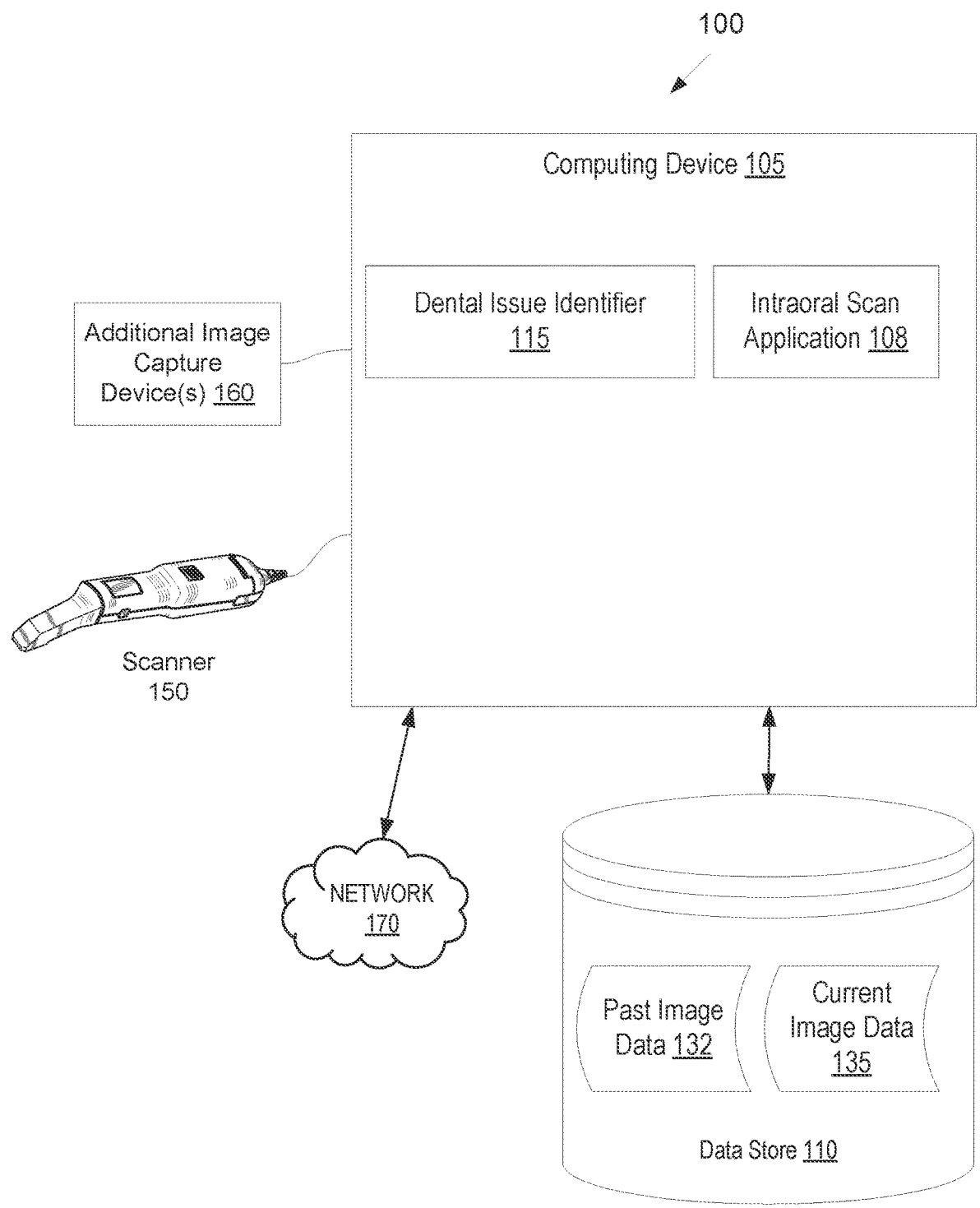
FIG. 1A illustrates one embodiment of a system for identifying dental issues, in accordance with an embodiment.

Described herein are methods and apparatuses for identifying changes that have occurred in a dental arch over time that have clinical significance. Many changes of clinical importance may occur to a dental arch over time, such as tooth movement, gum recession, gum swelling, tooth wear, tooth discoloration, changes in tooth translucency, gum discoloration, changes in occlusion, and so on. A single image or single intraoral scan may not be sufficient to identify dental issues. Additionally, a single image or single intraoral scan will not provide information such as whether gum recession or tooth wear has stopped or is continuing, a rate of such gum recession or tooth wear, and so on.

However, it can be difficult to detect clinical dental issues based on a comparison between different images or intraoral scans.

Image data such as the image data generated from an intraoral scan of a patient's dental arch often includes errors. For example, intraoral scanners have a limited field of view (FOV), and intraoral images from intraoral scanners are stitched together to form a three dimensional (3D) image or virtual model of a dental arch (or portion of a dental arch) that is much larger than the FOV. Such stitching together of the intraoral images causes errors to accumulate. The term virtual model as used herein refers to a model that is in a digital format (e.g., as opposed to a physical or real-world model). Virtual models may be 2D virtual models or 3D virtual models. If a virtual model is not specified as a 2D or 3D virtual model, then it may be either a 2D virtual model or a 3D virtual model. A virtual 3D model in embodiments may include a 3D surface as well as appearance properties mapped to each point of the 3D surface (e.g., the color of the surface on each point). Individual 3D scans and/or individual images may be taken during a scan and used to create the virtual 3D model.

The further apart two points are, the greater the accumulated error between them. Additionally, the curved shape of the dental arch and jaw causes specific error modes such as expansion of the distance between molar endings. When two 3D images or virtual models are produced, the accumulated errors may be different for each of these 3D images or virtual models. This can make comparison of these two images or virtual models difficult, and the differences from errors can drown out or hide clinically significant changes to the dental arch and render such clinically significant changes undetectable. Additionally, some clinically significant changes may obscure other smaller clinically significant changes. Accordingly, even in the absence of scanner inaccuracy or other error, real intraoral changes like tooth movement of a tooth can drown out or hide tooth wear for that tooth. For example, large-scale changes such as tooth movement or jaw expansion may hide smaller changes such as tooth wear or gum recession. Embodiments discussed herein identify and separate out the differences between images or virtual models of a dental arch that are attributable to scanner inaccuracy, and accurately identify additional differences between the images or virtual models that are clinically significant. Additionally, embodiments identify and separate out different classes of clinically significant changes to prevent any of those changes from being hidden by other clinically significant changes. Accordingly, small changes (such as those associated with tooth wear, gum recession and gum swelling) that may be clinically significant in dentistry are detectable in embodiments in spite of differences caused by scanner inaccuracy. Additionally, clinically significant changes are also detectable in embodiments in spite of larger clinically significant changes. Thus, false alarms may be reduced and missed detections of clinically significant changes may be avoided by limiting the changes to possible clinical changes, removing scanner inaccuracies, and/or separately identifying large and small scale clinically significant changes.

It is just as difficult to compare appearance changes (e.g., color changes, transparency changes, reflectivity changes, spots, etc.) on a tooth if that tooth is moving as it is to compare small scale changes (e.g., due to tooth wear, gum recession, etc.) for that tooth if that tooth is moving. Part of the difficulty in identifying appearance changes is scanner imperfections related to estimating appearance. Additionally, appearance detected by the scanner may be affected by external issues such as view angle, distance, amount of saliva, and so on. Such imperfections should also be compensated for. Embodiments discussed herein further enable such appearance changes to be detected even where there is scanner inaccuracy and where larger scale clinically significant changes have occurred (such as tooth movement) that might otherwise hide or obscure such appearance changes. In embodiments, a tooth motion is detected and compensated for, and after the compensation processing logic is able compare tooth appearance (e.g., tooth color) to determine changes in the tooth appearance and/or compute tooth wear. Such comparison may be performed using a generated model of "stationary" teeth where motion was compensated and cancelled out.

In one example embodiment, a method of identifying clinical dental issues includes making a comparison between first image data of a dental arch and second image data of the dental arch. The first image data may be generated based on a first intraoral scan of the dental arch performed at a first time by a first intraoral scanner and the second image data may be generated based on a second intraoral scan of the dental arch performed at a second time by the first intraoral scanner or a second intraoral scanner. The method further includes determining a plurality of spatial differences between a first representation of the dental arch in the first image data and a second representation of the dental arch in the second image data. The method further includes determining that a first spatial difference of the plurality of spatial differences is attributable to scanner inaccuracy of at least one of the first intraoral scanner or the second intraoral scanner and that a second spatial difference of the plurality of spatial differences is attributable to a clinical change to the dental arch. The method further includes generating a third representation of the dental arch that is a modified version of the second representation, wherein the first spatial difference is removed in the third representation, and wherein the third representation includes a visual enhancement that accentuates the second spatial difference. The visual enhancement may include a visual overlay (e.g., a color overlay) that identifies regions of the dental arch associated with the second difference. The visual enhancement may additionally or alternatively include an extrapolation of the spatial difference into the future to show a more extreme future difference.

In a further example embodiment, the method of identifying clinical dental issues may include making an additional comparison between the first image data and either the second image data and/or the third representation. The additional comparison may be performed to identify appearance differences (e.g., visual differences in color, hue, intensity, and so on) between the first image data and the second image data and/or third representation. These appearance differences may be divided into appearance differences attributable to scanner inaccuracy and appearance differences attributable to clinical changes. The appearance differences attributable to scanner inaccuracy may be removed, and the third representation may be updated to accentuate the appearance differences attributable to clinical changes of the dental arch.

Embodiments are discussed herein with reference to comparison of two representations of a dental arch (e.g., based on intraoral scans taken at two different times). However, it should be understood that more than two representations of a dental arch may be compared in embodiments. For example, in some embodiments three representations of a dental arch, four representations of a dental arch, or even more representations of a dental arch may be compared.

Such additional comparisons may be used to determine if a clinical problem is accelerating or decelerating. Additionally, such additional comparisons may be used to determine if a clinical problem that was previously sub-treatable (not severe enough to warrant treatment) has passed a threshold and should be treated. Additionally, additional comparisons using three or more representations of a dental arch may be used to improve detectability of slow changing clinical issues and distinguish such slow changing clinical issues from false alarms. In example, if n intraoral scans are performed (where n is an integer), then the results of each of the n scans may be compared either to the results of the preceding and subsequent scans or to the results of every other scan. For example, results of the second scan may be compared to results of the third scan and the first scan, results of the third scan may be compared to results the second scan and the fourth scan, and so on. This may reduce false alarms and improve detection.

FIG. 1A illustrates one embodiment of a system 100 for identifying clinical dental issues. In one embodiment, system 100 carries out one or more operations of below described methods 200, 300, 600, 800 and/or 1000. System 100 includes a computing device 105 that may be coupled to a scanner 150, an additional image capture device 160, a network 170 and/or a data store 110.

Computing device 105 may include a processing device, memory, secondary storage, one or more input devices (e.g., such as a keyboard, mouse, tablet, speakers, or the like), one or more output devices (e.g., a display, a printer, etc.), and/or other hardware components. Computing device 105 may be connected to data store 110 either directly (as shown) or via network 170. The network 170 may be a local area network (LAN), a public wide area network (WAN) (e.g., the Internet), a private WAN (e.g., an intranet), or a combination thereof. The computing device 105 may be integrated into the scanner 150 or image capture device 160 in some embodiments to improve mobility.

Data store 110 may be an internal data store, or an external data store that is connected to computing device 105 directly or via network 170. Examples of network data stores include a storage area network (SAN), a network attached storage (NAS), and a storage service provided by a cloud computing service provider. Data store 110 may include a file system, a database, or other data storage arrangement.

In some embodiments, a scanner 150 (e.g., an intraoral scanner) for obtaining three-dimensional (3D) data of a dental site in a patient's oral cavity is operatively connected to the computing device 105. Scanner 150 may include a probe (e.g., a hand held probe) for optically capturing three dimensional structures (e.g., by confocal focusing of an array of light beams). One example of such a scanner 150 is the iTero® intraoral digital scanner manufactured by Align Technology, Inc. Other examples of intraoral scanners include the 3M True Definition Scanner and the Cerec Omnicam manufactured by Sirona®.

The scanner 150 may be used to perform an intraoral scan of a patient's oral cavity. An intraoral scan application 108 running on computing device 105 may communicate with the scanner 150 to effectuate the intraoral scan. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the scanner 150 at a first position in the oral cavity, move the scanner 150 within the oral cavity to a second position while the video is being taken, and then stop recording the video. The scanner 150 may transmit the discrete intraoral images or intraoral video (referred to collectively as image data) to the computing device 105. Note that as used herein image data may be actual two-dimensional or three-dimensional images (e.g., discrete intraoral images or intraoral video), a representation of a dental arch (e.g., a virtual three-dimensional model of the dental arch), an x-ray image, a computed tomography (CT) image, or a combination thereof. Accordingly, the term image data may not actually include images in some embodiments. Computing device 105 may store the image data in data store 110. The image data may include past image data 132 generated by a scanner 150 at a first time and current image data 135 generated by the scanner 150 or an additional scanner at a second later time. Alternatively, scanner 150 may be connected to another system that stores the past image data 132 and/or current image data 135 in data store 110. In such an embodiment, scanner 150 may not be connected to computing device 105.

According to an example, a user (e.g., a practitioner) may subject a patient to intraoral scanning. In doing so, the user may apply scanner 150 to one or more patient intraoral locations. The scanning may be divided into one or more segments. As an example the segments may include a lower buccal region of the patient, a lower lingual region of the patient, a upper buccal region of the patient, an upper lingual region of the patient, one or more preparation teeth of the patient (e.g., teeth of the patient to which a dental device such as a crown or an orthodontic alignment device will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with scan being directed towards an interface area of the patient's upper and lower teeth). Via such scanner application, the scanner 150 may provide current image data (also referred to as scan data) 135 to computing device 105. The current image data 135 may include 2D intraoral images and/or 3D intraoral images.

The current image data 135 and past image data 132 may each be used to generate a virtual model (e.g., a virtual 2D model or virtual 3D model) of the patient's dental arch in some embodiments. Each virtual model may reflect the condition of the dental arch at a particular point in time. Each virtual model may include a 3D surface and appearance properties mapped to each point of the 3D surface (e.g., a color of the surface at each point). To generate a virtual model, intraoral scan application 108 may register (i.e., "stitch" together) the intraoral images generated from an intraoral scan session. In one embodiment, performing image registration includes capturing 3D data of various points of a surface in multiple images (views from a camera), and registering the images by computing transformations between the images. The images may then be integrated into a common reference frame by applying appropriate transformations to points of each registered image.

In one embodiment, image registration is performed for each pair of adjacent or overlapping intraoral images (e.g., each successive frame of an intraoral video) generated during an intraoral scan session. Image registration algorithms are carried out to register two adjacent intraoral images, which essentially involves determination of the transformations which align one image with the other. Image registration may involve identifying multiple points in each image (e.g., point clouds) of an image pair, surface fitting to the points of each image, and using local searches around points to match points of the two adjacent images. For example, intraoral scan application 108 may match points of one image with the closest points interpolated on the surface of the other image, and iteratively minimize the distance between matched points. Intraoral scan application 108 may also find the best match of curvature features at points of one image with curvature features at points interpolated on the surface of the other image, without iteration. Intraoral scan application 108 may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, intraoral scan application 108 may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Intraoral scan application 108 repeats image registration for all adjacent image pairs of a sequence of intraoral images to obtain a transformation between each pair of images, to register each image with the previous one. Intraoral scan application 108 then integrates all images into a single virtual 3D model by applying the appropriate determined transformations to each of the images. Each transformation may include a rigid body motion (e.g., rotations and/or translations).

In addition to current image data 135 and past image data 132, image data to be compared may additionally include multiple different instances of past image data 132. For example, image data may include first past image data based on a first intraoral scan taken at a first time, second past image data based on a second intraoral scan taken at a second time, and so on. Comparisons may be made between each of the image data. Alternatively, comparisons may be made between adjacent in time image data. For example, first past image data may be compared to second past image data and second past image data may additionally be compared to current image data in the above example. Each of the current image data 135 and past image data 132 may include additional collected information such as the time that the image data was generated (e.g., the time that a scan was performed), clinical verbal information (e.g., specific patient complaints at a time of scanning), scanner or model creation information (e.g., a type of scanner used to generate images from which a virtual 3D model was generated), and so on.

In addition to current image data 135 and past image data 132 including data captured by scanner 150 and/or data generated from such captured data (e.g., a virtual 3D model), image data may also include data from one or more additional image capture devices 160. The additional image capture devices 160 may include an x-ray device capable of generating standard x-rays (e.g., bite wing x-rays), panoramic x-rays, cephalometric x-rays, and so on. The additional image capture devices 160 may additionally or alternatively include an x-ray device capable of generating a cone beam computed tomography (CBCT) scan. Additionally, or alternatively, the additional image capture devices 160 may include a standard optical image capture device (e.g., a camera) that generates two-dimensional or three-dimensional images or videos of a patient's oral cavity and dental arch. For example, the additional image capture device 160 may be a mobile phone, a laptop computer, an image capture accessory attached to a laptop or desktop computer (e.g., a device that uses Intel® RealSense™ 3D image capture technology), and so on. Such an additional image capture device 160 may be operated by a patient or a friend or family of the patient, and may generate 2D or 3D images that are sent to the computing device 105 via network 170. Additionally, an additional image capture device 160 may include an infrared (IR) camera that generates near IR images. Accordingly, current image data 135 and past image data 132 may include 2D optical images, 3D optical images, virtual 2D models, virtual 3D models, 2D x-ray images, 3D x-ray images, and so on.

Dental issue identifier 115 compares current image data 135 of a dental arch to past image data 132 of the dental arch to identify changes that have occurred to the dental arch. However, detected differences include both differences caused by scanner inaccuracy as well as differences caused by clinical changes such as tooth wear (also referred to as tooth erosion), gum recession, gum swelling, occlusion (e.g., bite surfaces) and so on. Dental issue identifier 115 identifies those differences caused by scanner inaccuracy and filters them out. Additionally, dental issue identifier 115 may apply a low pass filter to smooth out very high noise-like errors (e.g., to smooth out errors having a frequency of higher than 100 microns). The remaining differences that are caused by clinical changes to the dental arch may then be identified, classified and displayed. The dental issue identifier 115 is discussed in greater detail below with reference to FIG. 1B.

In embodiments, a first intraoral scan that produces past image data 132 is performed at the start of orthodontic treatment, and a second intraoral scan that produces the current image data 135 is performed during the orthodontic treatment (e.g., during an intermediate stage of a multi-stage orthodontic treatment plan). Alternatively, or additionally, other image data may be generated during at the start of the orthodontic treatment and during the orthodontic treatment. Moreover, multiple scans may be performed during the orthodontic treatment.

The task of identifying changes of clinical significance is made more complex during an orthodontic treatment. For such an orthodontic treatment, teeth may be moved according to a treatment plan and at the same time unplanned tooth wear, gum recession, tooth chips, and so on may occur. The planned tooth changes may occlude the unplanned changes of clinical significance in some instances. Additionally, other types of treatments may also increase the complexity of identifying changes of clinical significance. For example, a restorative treatment may cause one or more teeth to change their shape, which may occlude unplanned changes. Additionally, in a hygienist treatment some tartar may be removed, which may change interproximal tooth regions as well as some gum regions. These differences caused by the hygienist treatment (e.g., tooth cleaning) or other types of treatment can be taken into account to determine whether a change is of clinical significance. For example, information such as a date of a hygienist treatment or a date and/or tooth shape of a restorative treatment may be used to help classify a change as a clinical change or non-clinical change.

A multi-stage orthodontic treatment plan may be for a multi-stage orthodontic treatment or procedure. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, aligners, or functional appliances. Different aligners may be formed for each treatment stage to provide forces to move the patient's teeth. The shape of each aligner is unique and customized for a particular patient and a particular treatment stage. The aligners each have teeth-receiving cavities that receive and resiliently reposition the teeth in accordance with a particular treatment stage.

The multi-stage orthodontic treatment plan for a patient may have initially been generated by a dental practitioner (e.g., an orthodontist) after performing a scan of an initial pre-treatment condition of the patient's dental arch, which may be represented in the past image data 132. The treatment plan may also begin at home (based on a patient scan of himself) or at a scanning center. The treatment plan might be created automatically or by a professional (including an Orthodontist) in a remote service center. The scan may provide 3D surface data (e.g., surface topography data) for the patient's intraoral cavity (including teeth, gingival tissues, etc.). The 3D surface data can be generated by directly scanning the intraoral cavity, a physical model (positive or negative) of the intraoral cavity, or an impression of the intraoral cavity, using a suitable scanning device (e.g., a handheld scanner, desktop scanner, etc.). Image data from the initial intraoral scan may be used to generate a virtual three-dimensional (3D) model or other digital representation of the initial or starting condition for the patient's upper and/or lower dental arches.

The dental practitioner may then determine a desired final condition for the patient's dental arch. The final condition of the patient's dental arch may include a final arrangement, position, orientation, etc. of the patient's teeth, and may additionally include a final bite position, a final occlusion surface, a final arch length, and so on. A movement path of some or all of the patient's teeth and the patient bite changes from starting positions to planned final positions may then be calculated. In many embodiments, the movement path is calculated using one or more suitable computer programs, which can take digital representations of the initial and final positions as input, and provide a digital representation of the movement path as output. The movement path for any given tooth may be calculated based on the positions and/or movement paths of other teeth in the patient's dentition. For example, the movement path can be optimized based on minimizing the total distance moved, preventing collisions between teeth, avoiding tooth movements that are more difficult to achieve, or any other suitable criteria. In some instances, the movement path can be provided as a series of incremental tooth movements that, when performed in sequence, result in repositioning of patient's teeth from the starting positions to the final positions.

Multiple treatment stages may then be generated based on the determined movement path. Each of the treatment stages can be incremental repositioning stages of an orthodontic treatment procedure designed to move one or more of the patient's teeth from a starting tooth arrangement for that treatment stage to a target arrangement for that treatment stage. One or a set of orthodontic appliances (e.g., aligners) are then fabricated based on the generated treatment stages (e.g., based on the virtual 3D models of the target conditions for each of the treatment stages). For example, a set of appliances can be fabricated, each shaped to accommodate a tooth arrangement specified by one of the treatment stages, such that the appliances can be sequentially worn by the patient to incrementally reposition the teeth from the initial arrangement to the target arrangement. The configuration of the aligners can be selected to elicit the tooth movements specified by the corresponding treatment stage.

The current image data 135 received during an intermediate stage in the multi-stage orthodontic treatment plan may be compared by dental issue identifier 115 to the past image data 132. Based on the comparison, dental issue identifier 115 determines clinical changes that have occurred to the dental arch, and compares those clinical changes that are detected to expected clinical changes that are specified in the orthodontic treatment plan. Any deviation between the actual condition of the patient's dental arch and the planned condition of the patient's dental arch for the current treatment stage may then be determined. The dental practitioner may then take one or more corrective actions based on the detected deviation.

In some embodiments, current image data 135 received during an intermediate stage in a multi-stage orthodontic treatment plan may be used to analyze a fit of a next aligner based on the actual current condition of the dental arch (e.g., based on current teeth positions, occlusion, arch width, and so on). If the next aligner will not have an optimal fit on the patient's dental arch (e.g., will not fit onto the dental arch or will fit but will not apply the desired forces on one or more teeth), then new aligners may be designed based on updating the treatment plan staging.

Figure 1B:
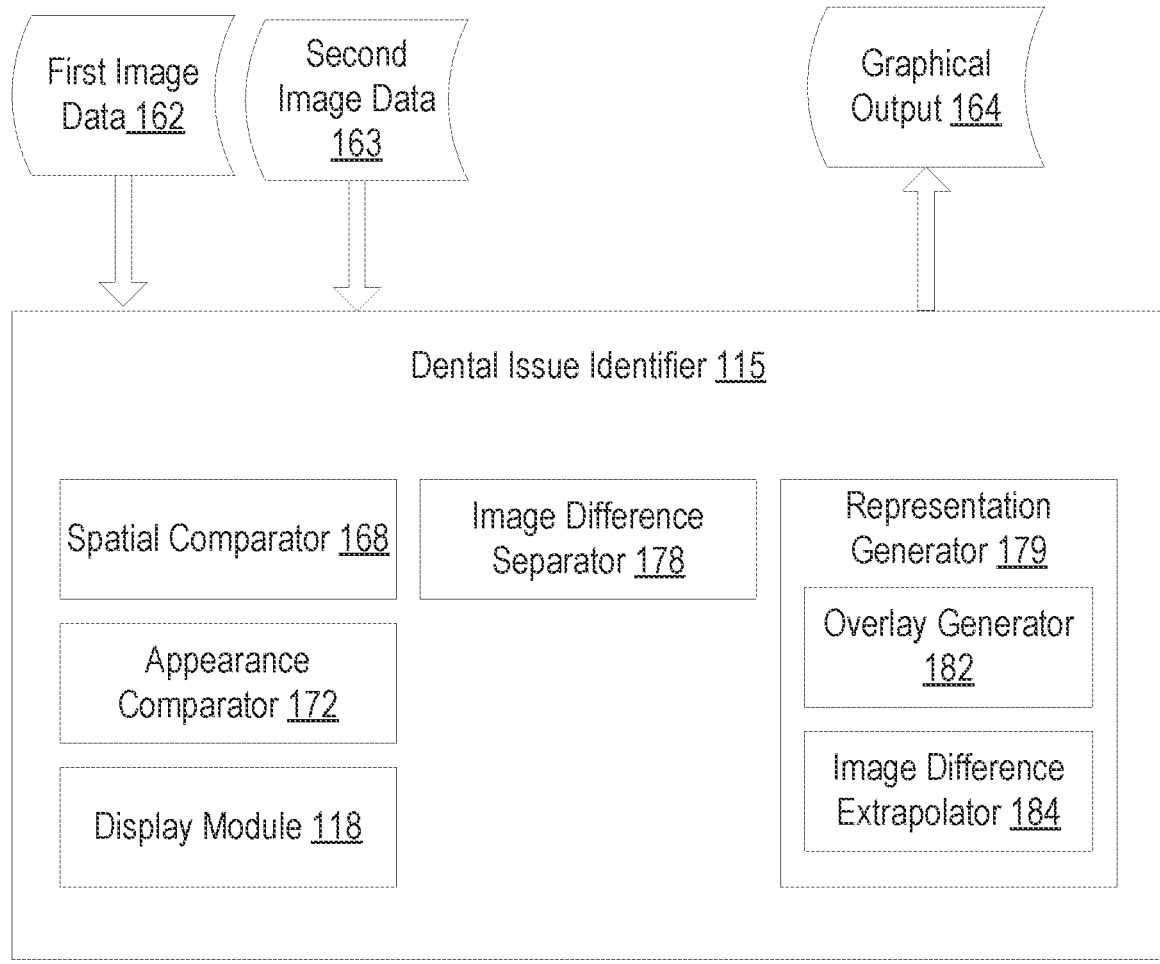
FIG. 1B illustrates one embodiment of a dental issue identifier, in accordance with an embodiment.

FIG. 1B illustrates one embodiment of a dental issue identifier 115, in accordance with an embodiment. In one embodiment, the dental issue identifier 115 includes a spatial comparator 168, an appearance comparator 172, an image difference separator 178, a representation generator 179 and a display module 118. Alternatively, one or more of the spatial comparator 168, appearance comparator 172, image difference separator 178, representation generator 179 and/or display module 118 may be combined into a single module or further divided into additional modules.

Spatial comparator 168 compares spatial information from first image data 162 with spatial information from second image data 163. The first image data 162 may have been generated from an intraoral scan taken at a first time and may be considered a reference surface. The second image data 163 may have been generated from an intraoral scan taken at a second time and may be considered a test surface. The first image data 162 may be or include a first virtual 3D model of the dental arch that represents a condition of the dental arch at the first time, and the second image data 163 may be or include a second virtual 3D model of the dental arch that represents a condition of the dental arch at the second time. A representation of the dental arch (e.g., a first 3D virtual model) in the first image data 162 may be compared with a representation of the dental arch (e.g., a second virtual 3D model) in the second image data 163.

Spatial comparison of the first image data 162 with the second image data 163 may include performing image registration between the first image data 162 and second image data 163. The image registration involves determination of the transformations which align one image with the other. Image registration may involve identifying multiple points, point clouds, edges, corners, surface vectors, etc. in each image of an image pair, surface fitting to the points of each image, and using local searches around points to match points of the two images. For example, spatial comparator 168 may match points of one image with the closest points interpolated on the surface of the other image, and iteratively minimize the distance between matched points. Spatial comparator 168 may select the points based on a random sampling of surface vertices, based on binning of vertices to a voxel grid and averaging each voxel, based on feature detection (e.g., detecting tooth cusps), and/or based on other techniques. Spatial comparator 168 may also find the best match of curvature features at points of one image with curvature features at points interpolated on the surface of the other image, with or without iteration. Spatial comparator 168 may also find the best match of spin-image point features at points of one image with spin-image point features at points interpolated on the surface of the other image, with or without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Surface patches may be selected using various techniques, such as by selecting parts of a surface that are less than a threshold distance (e.g., in millimeters) away from a selected point (where a connected component is generated that includes the point itself), by performing tooth segmentation and associating points with a tooth crown that includes a selected point or a part of such a crown, and so on. Various matching techniques may also be employed by the image registration algorithms.

In one embodiment, spatial comparator 168 may determine a point match between images, which may take the form of a two dimensional (2D) curvature array. A local search for a matching point feature in a corresponding surface patch of another image is carried out by computing features at points sampled in a region surrounding the parametrically similar point. One matching technique that may be used includes running an iterative closest point (ICP) algorithm from several staring positions. Another matching technique includes detecting a number of orientation-independent surface features on test surfaces of one image and reference surfaces on the other image. For each feature on a test surface, spatial comparator 168 may find all similar features on the reference surface and vote for particular transforms that would align features on the test surface with the features on the reference surface. The transformation with the most votes may then be picked, and a result may be refined using an ICP algorithm.

Spatial comparator 168 may validate the quality of detected matches with a suitable method and discard points that did not match well. One suitable method for validation includes computing a percentage of surface area on a tested part of the test surface that is less than a threshold distance (e.g., in millimeters) away from the reference surface after alignment. A match may be validated if the size of the surface area that matched is larger than a size threshold. Another suitable method for validation includes computing an average or median distance between vertices of a tested part of the test surface and the reference surface after alignment. If the average or median between vertices is less than a threshold distance, then validation may be successful.

Spatial comparator 168 may compute a mean and/or median alignment of the entire set of matches. Spatial comparator 168 may detect and remove outliers that suggest variants of alignment of the test surface and reference surface that are too different from the mean or median alignment of the entire set of matches by using an appropriate method. For example, surface patches for which the alignment of the test surface to the reference surface has an alignment value that differs from the mean or median by more than a threshold may be too different. One appropriate method that may be used is the random sample consensus (RANSAC) algorithm. If two surfaces are not comparable, then spatial comparator 168 will determine that the registration has failed because the number of surviving points would be too small to reasonably cover the entire test surface. This might happen, for example, if input data contained a mistake (e.g., a user tried to match an intraoral scan of one person to an intraoral scan of another person). Spatial comparator 168 may check for such a condition and report an error if this occurs.

A result of the surface matching may be a dense set of pairs of matching points, with each pair corresponding to a region on the test surface and a matching region on the reference surface. Each such region is also associated with a point, so each pair can also be viewed as a pair of a point on the test surface and a matching point on reference surface. An ordered set of these points on a test surface is a point cloud on the test surface, and a set of matching points on a reference surface ordered in the same way is a matching point cloud on the reference surface.

A suitable algorithm may be used to compute an approximate alignment of a test point cloud to a reference point cloud. One example of such a suitable algorithm includes the least-squares minimization of distance between test and reference point clouds. After approximate alignment via a rigid transformation of the test surface, test and reference point clouds won't coincide exactly. A suitable algorithm may be used to compute a non-rigid transformation such as a piecewise-smooth warp space transformation that smoothly deforms a 3D space such that 1) this deformation is as smooth as possible and b) the test point cloud after application of the warp transformation is much better aligned with the reference point cloud. Possible implementation options include, but are not limited to, radial basis function interpolation, thin-plate splines (TPS) and estimating teeth movements and propagating them to a nearby space.

Accordingly, once corresponding point sets are determined between surface patches of the two images, determination of the transformation between the two sets of corresponding points in two coordinate frames can be solved. Essentially, an image registration algorithm may compute a transformation between two images that will minimize the distances between points on one surface, and the closest points to them found in the interpolated region on the other image surface can be used as a reference. The transformation may include rotations and/or translational movement in up to six degrees of freedom. Additionally, the transformation may include deformation of one or both of the images (e.g., warp space transformations and/or other non-rigid transformations). A result of the image registration may be one or more transformation matrix that indicates the rotations, translations and/or deformations that will cause the one image to correspond to the other image.

A result of the spatial comparison performed by spatial comparator 186 may include an alignment transformation (e.g., rigid transformation in position and/or orientation to achieve a rigid body alignment) and a warp space transformation or other non-rigid transformation (e.g., smooth deformation of 3D space). Image difference separator 178 may use such information to determine differences between points, point clouds, features, etc. on a first representation of the dental arch (reference surface) from the first image data 162 and a second representation of the dental arch (test surface) from the second image data 163. Image difference separator 178 may then distinguish between differences that are attributable to scanner inaccuracy and differences that are attributable to clinical changes in the dental arch.

Differences between the first representation of the dental arch and the second representation of the dental arch generally occur in different spatial frequency domains. For example, relatively smooth changes that occur in arch length and jaw width are generally caused by scanner inaccuracy and happen with a low spatial frequency and a high magnitude. For example, the human jaw typically does not change in width over time for an adult. However, for intraoral scanners with a limited FOV, it is common for the measured jaw or arch width (distance between last molars of the jaw) to vary between scans. Other types of changes that have clinical significance generally occur with a much higher spatial frequency and a much lower magnitude. As used herein, spatial frequency means changes in a vector field with lateral changes in position, where each vector in the vector field represents where a point of the test surface would move after applying the rigid and non-rigid transformations. Differences between the first representation and the second representation that change slowly with lateral changes in position have a low spatial frequency or lateral frequency, and are global differences that may affect the entire dental arch or a large region of the dental arch. These would show as a smooth vector field, where the vectors of points have similar values to vectors of nearby points.

Scanner errors may also have a very high spatial frequency or a very fine scale. This may be noise introduced by the scanner, and may be filtered out with a low pass filter. Spatial differences with a very high spatial frequency (a very small scale) may be those spatial differences with a spatial frequency that exceeds a frequency threshold. Spatial differences attributable to clinical changes may have a spatial frequency that is lower than the frequency threshold.

Changes of clinical significance are local changes that occur only in a small region on the dental arch. Changes of tooth wear happen on a scale of a small tip of a tooth, and occur only at that region. Accordingly, tooth wear has a high spatial frequency. Additionally, the magnitude of tooth wear is generally small (e.g., fractions of a millimeter). Similarly, changes in gum line (e.g., gum recession) happen at the gum line and in a particular direction (perpendicular to the gum line). Additionally, the magnitude of gum recession and gum swelling can also be quite small (e.g., fractions of a millimeter). Tooth movement happens at the scale of the tooth size. The known scales of each of these types of clinical changes can be used to separate differences between dental arch representations caused by scanner inaccuracy and clinical changes, and can be further used to separate out and/or classify each of the different types of clinical changes.

To separate the differences between representations of the dental arch that are based on scanner inaccuracy, the smooth or low frequency changes can be filtered out, such as by applying a low pass filter. Such smooth changes can be identified by the low pass filter and then removed from the test surface (representation of the dental arch from the second image data). In other words, this error or difference may be subtracted from the test surface for a better fit between the test surface and reference surface. The low pass filter may filter out spatial differences having a spatial frequency that is higher than a frequency threshold.

In one embodiment, alignment transformation (e.g., transformation in position and/or orientation) and warp space transformation (e.g., deformation) computed from a point cloud may be applied to the entire test surface. A magnitude of the warp space transformation may be reported as a "global" component of a surface difference and visualized with a suitable method. Representation generator 179 may generate a representation of the aligned and warped second image data (e.g., a third representation of the dental arch that is computed based on applying the alignment transformation and the warp space transformation to a second representation of the dental arch from the second image data 163). Suitable methods include a per-point coloring of the test surface according to a magnitude of the warp movement at this point and coloring of an entire tooth crown according to a magnitude of its movement. Such global component of the surface difference may be the surface difference that is attributable to scanner inaccuracy.

In one embodiment, a suitable algorithm may be used to compute residual differences between the aligned and warped test surface and the reference surface. This residual may be reported as a "local" component of the surface difference. A possible implementation option includes computing a distance to a nearest point of reference surface for each point of an aligned and warped test surface and coloring the test surface accordingly (e.g., coloring based on a magnitude of the distance, where a first color may be used for a first distance magnitude, a second color may be used for a second distance magnitude, and so on). Another possible implementation option includes performing an additional comparison as set forth above to split the remaining differences into additional levels (e.g., into tooth movement, changes in gingival shape, changes to the tooth surface, changes in tooth crowding, changes in tooth spacing, occlusion changes, orthodontic relapse, changes to proximal contacts, and so on).

To split the differences into different levels, one or more filters or filtering operations may be applied to separate the differences into differences of different spatial frequencies or scale. These filters may be applied based on the registration information output by spatial comparator 168 as described above. Alternatively, or additionally, image difference separator 178 may invoke spatial comparator 168 to repeat the above described operations with regards to image comparison and registration using the third representation previously output by the spatial comparator 168 as a starting point rather than using the second image data 163 as the starting point. One or more filters such as low pass filters may then be applied to distinguish each level of local changes.

Each of the applied filters may be low pass filters that look for differences in surfaces at points that are "similar" to differences at nearby points (e.g., by performing approximate rigid body transformation, by fitting a smooth deformation function to test data, or by segmenting a virtual 3D model into teeth and computing motion of each tooth separately). Spatial comparator 168 and/or difference separator 178 may compute a "low-frequency" component, then effectively "subtract" that low-frequency component from the surface or otherwise compensate for the computed low-frequency differences between the target surface and the reference surface. Subtraction of the low-frequency component from the data may effectively form a complimentary high-pass filter. This process may be performed repeatedly, with each application of the process detecting a lowest frequency component that has not yet been filtered out.

For example, a first low pass filter may be applied to filter out all differences attributable to scanner inaccuracies that cause a detected difference in arch length or jaw width. Then another low pass filter may be applied to this already filtered data. With some lower-frequency components already filtered out, the net result is the same as if a bandpass filter for a specific range of spatial frequencies was applied to original data. For example, subtraction of the error component yields data that corresponds to application of a high-pass filter with higher cutoff frequency to the original surface. This process can be repeated as many times as desired to generate a sequence of differences or changes corresponding to different bands of spatial frequencies. For example, a second low pass filter may be applied to filter out all differences attributable to tooth movement. A third low pass filter may then be applied to filter out all differences attributable to gum recession or tooth wear, and so on. Accordingly, a chained sequence of filters may be applied, where output of a low-pass filter is fed as an input to another low-pass filter with a higher spatial frequency cutoff.

Embodiments split the data into non-overlapping bands of frequencies. Differences may be classified based on their scale or spatial frequency. For example, the spatial differences may be classified into a tooth movement classification, a tooth wear classification, a gum recession classification and/or a gum swelling classification.

Another technique that may be used to separate the differences into different classifications or categories is applying specific rules or algorithms to the first representation of the dental arch in the first image data and the third representation of the dental arch that is output by the spatial comparator 168. Each rule or algorithm may be configured to detect a particular type of clinical change. One or more of the rules or algorithms may detect specific changes based on a segmentation of the teeth and gums. Accordingly, the following examples may be performed after segmentation has been performed for the teeth and gums. For example, a gum recession detection rule may apply feature detection techniques to identify the gum line and the teeth in the dental arch in both representations. The gum recession detection rule may then measure a minimal distance between the gum line and peaks of each of the teeth in both representations.

These minimal distance measurements may then be compared between the representations. If, for example, the detected distance between the gum line and the peak of tooth 1 is greater in the third representation of the dental arch than in the first representation of the dental arch, then gum recession is identified. The distance measured in the first representation may be subtracted from the distance in the third representation to measure the actual amount of gum recession. A rate of recession may then be determined by determining the amount of time that elapsed between generation of the first image data 162 and the second image data 163, and the distance may be divided by the elapsed time to compute a rate of the gum recession.

In another example, a tooth movement detection rule may detect tooth movement. This may include first performing feature detection techniques to identify individual teeth. For each tooth, a change in position and orientation of the tooth between the first representation and the third representation may be determined based on the performed image registration. The change in position and orientation may be divided into different types of tooth movement, including lateral movement along different axes, movement into the jaw or away from the jaw, rotations about various axes, and so on. Each type of tooth movement may be measured and displayed. Additionally, a rate of movement may be determined based on dividing the magnitude of the movement by the elapsed time between the taking of the first image data and the taking of the second image data.

In some instances, the second image data 163 may be generated at an intermediate stage in orthodontic treatment. In such instances, there may be planned movement for various teeth. The actual detected tooth movement may be compared to the planned tooth movement to determine if the treatment is progressing as planned. Various thresholds may be applied to the tooth movements to determine this information.

Figure 11:
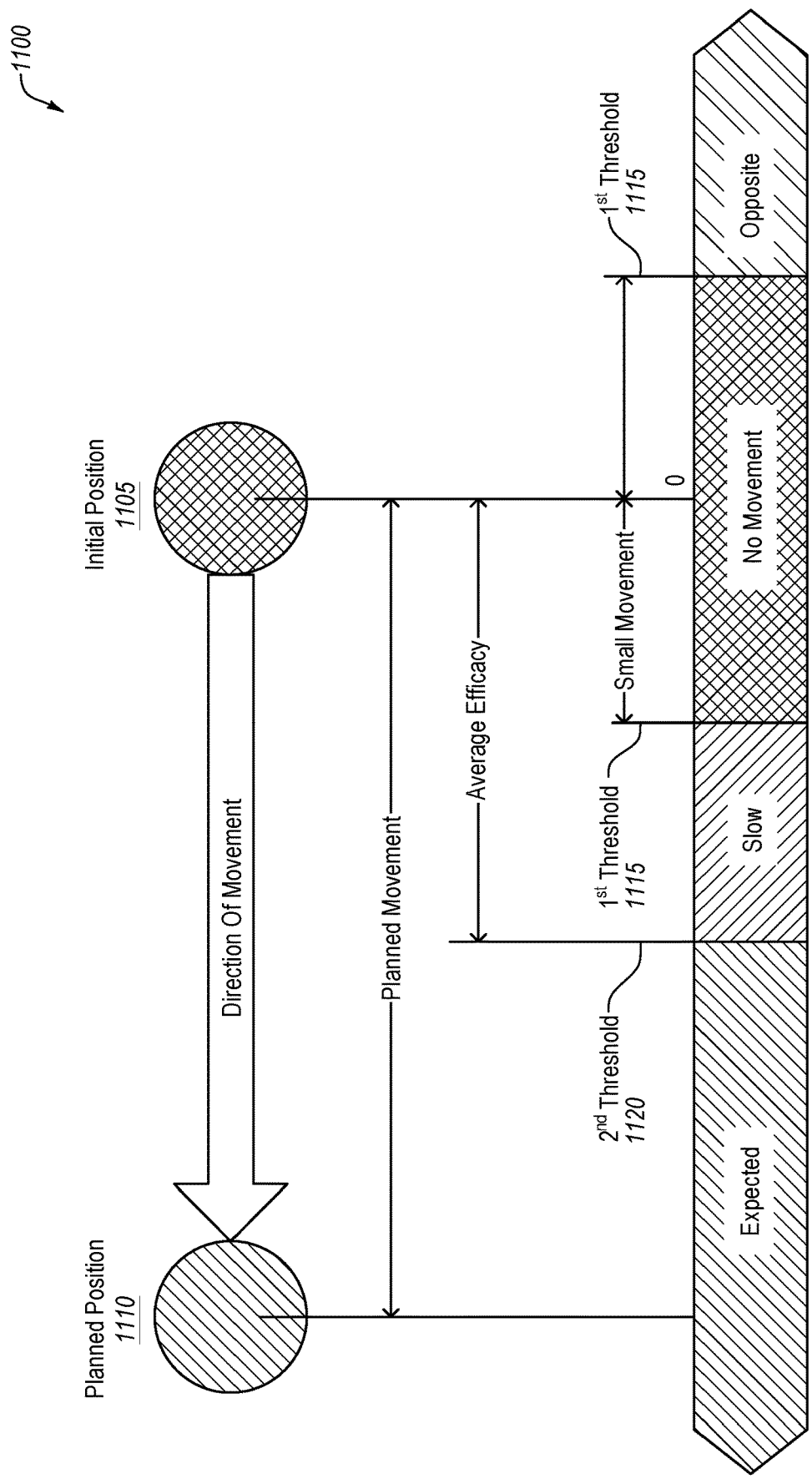
FIG. 11 is a diagram illustrating labeling of differences between actual tooth movement and planned tooth movement for a dental arch, in accordance with an embodiment.

FIG. 11 illustrates a chart 1100 showing different types of tooth movement. A treatment plan may call for a particular amount of tooth movement between an initial position 1105 and a planned position 1110 at an intermediate treatment stage. For translational movement the planned movement may be reflected in terms of distance (e.g., mm or inches) and for rotational movement the planned movement may be reflected in terms of degrees of rotation. Translational movement can include movement in a plane defined by the arch (e.g., movement along the arch that affects the separation between teeth) and can additionally or alternatively include movement outside of the plane (e.g., raising a tooth or lowering a tooth). If the actual tooth position deviates from the initial position 1105 by less than a first threshold 1115 (compliance threshold), then it may be determined that the tooth has not changed position. It may be determined that the tooth has not moved if the tooth movement is within the first threshold 1115 in the planned direction of movement and/or in an opposite direction of movement from the planned direction of movement. If tooth movement was less than planned and the actual tooth position exceeds the first threshold 1115 but is less than a second threshold 1120, then it may be determined that the tooth movement was less than planned. Alternatively, or additionally, the threshold may be based on a difference between a planned movement and an actual movement (e.g., if actual tooth position deviated from planned tooth position by more than a threshold amount, then it may be determined that the tooth movement was less than planned. If the detected movement exceeds the second threshold 1120, then tooth movement may be normal. Alternatively, or additionally, if the actual tooth movement deviates from the planned tooth movement by less than a threshold, then the tooth movement may be identified as normal. If the actual position shows movement in an opposite direction from the planned movement and exceeds the first threshold 1115, then it may be determined that tooth movement opposite to what was planned has been achieved.

FIG. 12 illustrates a table showing which teeth have positions that are in compliance with an orthodontic treatment plan and which teeth have positions that deviate from the orthodontic treatment plan, in accordance with an embodiment. As shown, the table includes a different row for each tooth, and different columns for each type of movement that is measured for the teeth. The tooth rows may be labeled by tooth number or tooth ID. The different types of tooth motion that are measured include bucco-lingual translational motion, mesio-distal translational motion, intrusion/extrusion tooth motion, angulation, inclination, and rotation. Angulation, inclination and rotation may each be considered as rotation about a different axis, and may be measured in degrees or rotation. The table shows the achieved tooth motion and planned tooth motion for each type of tooth motion. Additionally, the table includes an alert column that indicates any clinical signs that have been identified.

Computed difference data from several levels can be represented separately for each level or combined to show several levels at once in the third representation generated by representation generator 179. This data can also be filtered to hide insignificant changes and simplify analysis by highlighting regions of significant change.

Returning to FIG. 1B, representation generator 179 may generate a virtual 2D or 3D model of the patient's dental arch, or may generate a visualization of a virtual 2D or 3D model output by spatial comparator 168 and/or image difference separator 178. For example, representation generator 179 may generate a modified version of the third representation generated by the spatial comparator 168 or image difference separator 178. Alternatively, representation generator 179 may generate a generic image of a dental arch. An overlay generator 182 of the representation generator 179 may generate a graphical overlay (e.g., a color overlay) that marks regions of the dental arch for which image differences associated with clinical changes have been identified. For example, a first color (e.g., purple) may be used to indicate teeth associated with tooth movement opposite to what was planned, a second color (e.g., yellow) may be used to indicate teeth associated with tooth movement that is less than planned, a third color (e.g., green) may be used to indicate teeth that have moved as planned, and a fourth color (e.g., blue) may be used to indicate teeth associated with tooth movement that is greater than planned. The graphical overlay may also color in regions of the gums where recession has occurred with a particular color, regions of the gums where swelling has occurred with another color, teeth (or regions of teeth) that have been worn down with another color, and so on.

Figure 13:
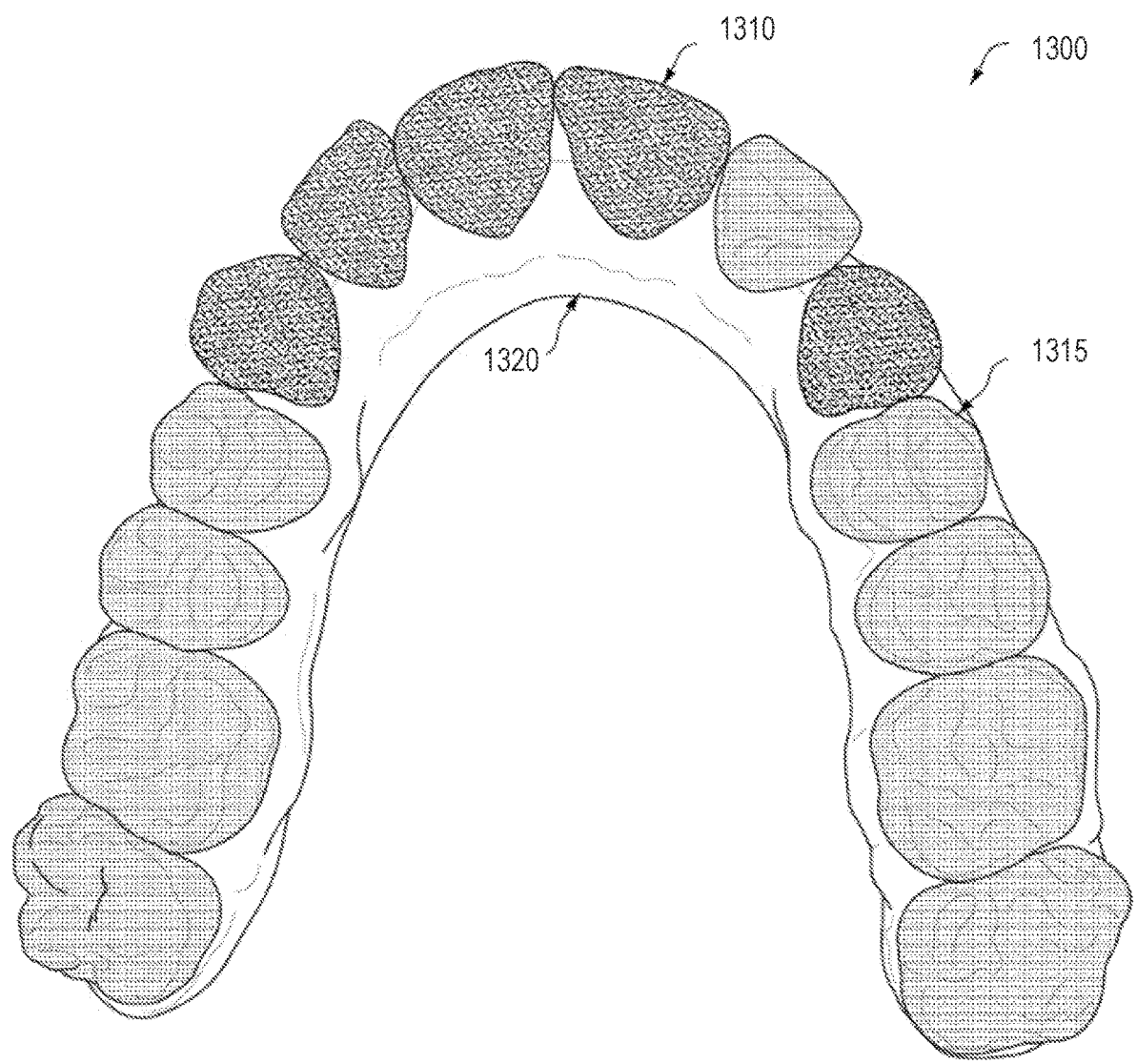
FIG. 13 illustrates a dental arch with a visual overlay indicating which teeth have moved less than expected and which teeth have moved as expected, in accordance with an embodiment.

FIG. 13 illustrates a virtual model of a patient's dental arch 1300 in which the teeth are color coded (or coded based on fill pattern) based on a detected clinical change that was detected for those teeth (or lack thereof) between current image data and past image data. As shown, teeth that have moved as planned 1315 are shown with a first color and/or other marking (e.g., green and/or a first hatching) and teeth that have moved less than planned are shown with a second color and/or other marking (e.g., orange or yellow and/or a second hatching). Additionally, gums 1320 may be shown with a third color and/or other marking (e.g., red).

Other types of labels or flags may be used to present and/or call out the various clinical signs, such as numerical labels, flags with text labels, and so on. These additional types of labels and/or flags may be used instead of or in addition to a color overlay or other visual overlay.

Figure 14A:
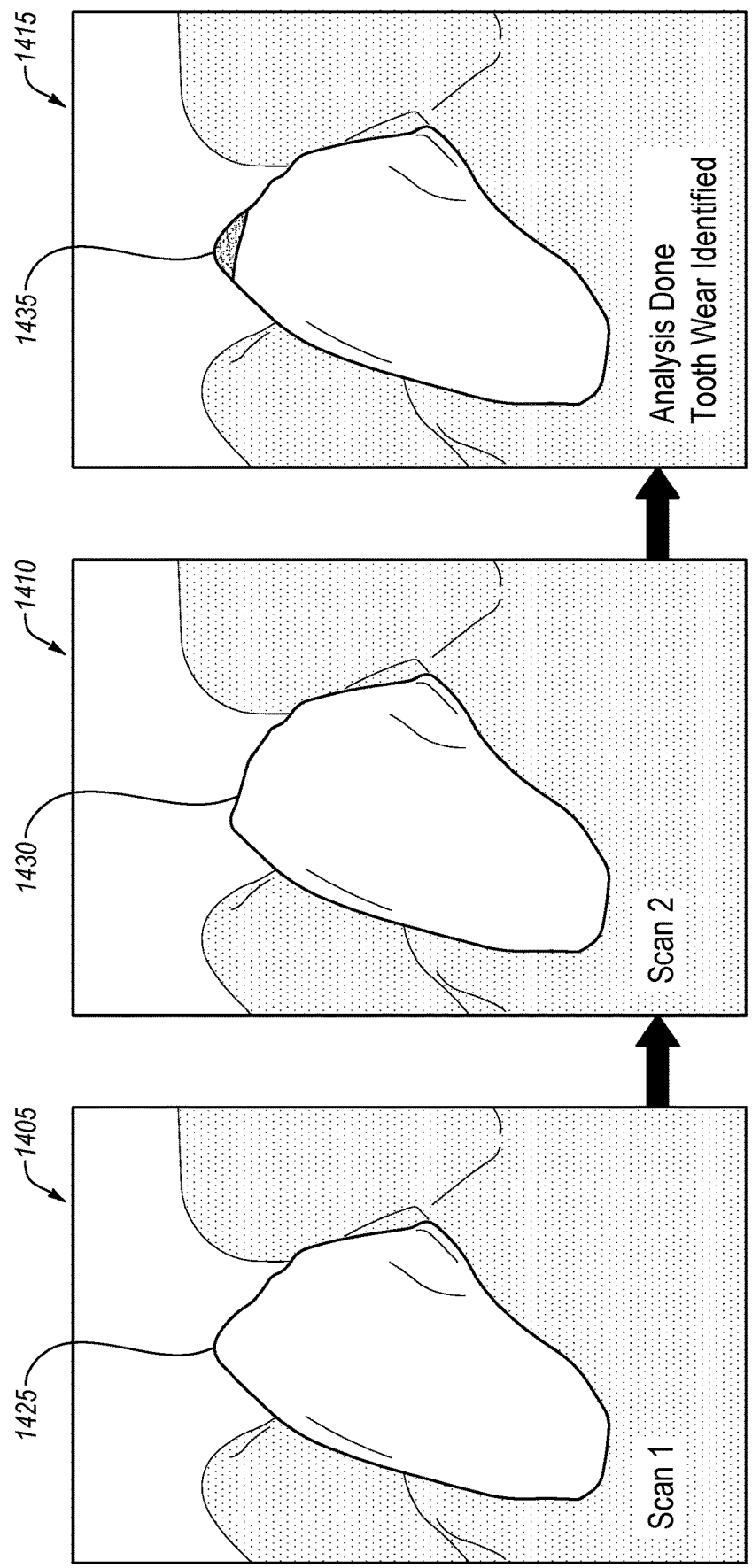
FIG. 14A illustrates a comparison between two different scans of a dental arch, in accordance with an embodiment.

FIG. 14A illustrates a comparison between two different scans of a dental arch, in accordance with an embodiment. As shown, a first scan 1405 is compared to a second scan 1410 in the manner described above. As a result of image registration, a past condition of a tooth 1425 is compared to a current condition of the tooth 1430. Based on the comparison, a representation of the dental arch 1415 that includes the tooth is generated. The representation of the tooth includes a highlighted or accentuated region 1435 that shows an amount of the tooth that has been worn away between the first scan 1405 and the second scan 1410.

Referring back to FIG. 1B, representation generator 179 may include an image difference extrapolator 184. Image difference extrapolator 184 may compute a magnitude of a difference between the first representation of the dental arch from the first image data 162 and a third representation of the dental arch as generated based on a comparison between the first image data 162 and the second image data 163. In one embodiment, image difference extrapolator 184 applies one or more color filters (and/or other appearance filters) to normalize aspects of the appearance between representations of the dental arch due to scanner differences.

As indicated above, first image data 162 and second image data 163 may each have a time stamp. Additionally, further image data may also be compared against the first image data and/or second image data and may also have time stamps. Image difference extrapolator 184 additionally determines an amount of time that separates the first image data 162 and the second image data 163. Additionally, image difference extrapolator 184 may determine amounts of time that separate the first image data 162 and second image data 163 from the further image data and/or amounts of time that separate the further image data from each other. Based on this information, image difference extrapolator 184 determines a rate of change associated with the difference. Image difference extrapolator 184 may apply the rate of change to the third representation to determine a predicted change to a region of the dental arch at a future date. Representation generator 179 may then generate a new representation of the dental arch that includes extrapolated changes to regions of the dental arch that are computed by image difference extrapolator. This representation may accentuate and exaggerate the changes of clinical significance to call them to the attention of the dental practitioner.

Additionally, after determining a rate of chance, image difference extrapolator 184 may estimate a time when a sub-clinical issue may evolve into a problem (into an issue of clinical significance). For example, image difference extrapolator 184 may compare a clinical change to a severity threshold. If the clinical change is below the severity threshold, then it may represent a sub-clinical issue and may not be significant enough to treat presently. However, over time that sub-clinical issue may develop in to a clinical issue. Accordingly, the rate of change may be applied to determine a future time at which the sub-clinical issue might become a clinical issue. Additional image data may be taken at the future time to determine whether the sub-clinical issue has developed into a clinical issue.

In an example, assume that a tooth wear problem is detected with a wear rate of 0.1 mm per month. The wear rate may not be critical yet, but it may present a problem in a year after 1.2 mm of enamel has been worn off. Alternatively, the identified wear rate of 0.1 mm per month may be a false alarm. Without additional data points, it may be difficult to distinguish between a false alarm and a clinical issue. Accordingly, image difference extrapolator 184 may determine a recommended future time to generate next image data and re-evaluate the possible tooth wear problem. Additional image data may be generated at the recommended future time, and the above discussed operations may be performed to determine clinical changes between the additional image data and the second image data 163. If the tooth wear in the above example has continued, then the sub-clinical issue may be identified as a clinical issue. If the tooth wear has not continued, then the sub-clinical issue may be identified as a false alarm.

If the further or additional image data is used (e.g., more than just the first image data 162 and second image data 163), then a determination may be made as to whether the rate of change for the one or more of the changes of clinical significance is accelerating or decelerating. This may be used to more accurately predict a future condition of clinical significance.

Figure 14B:
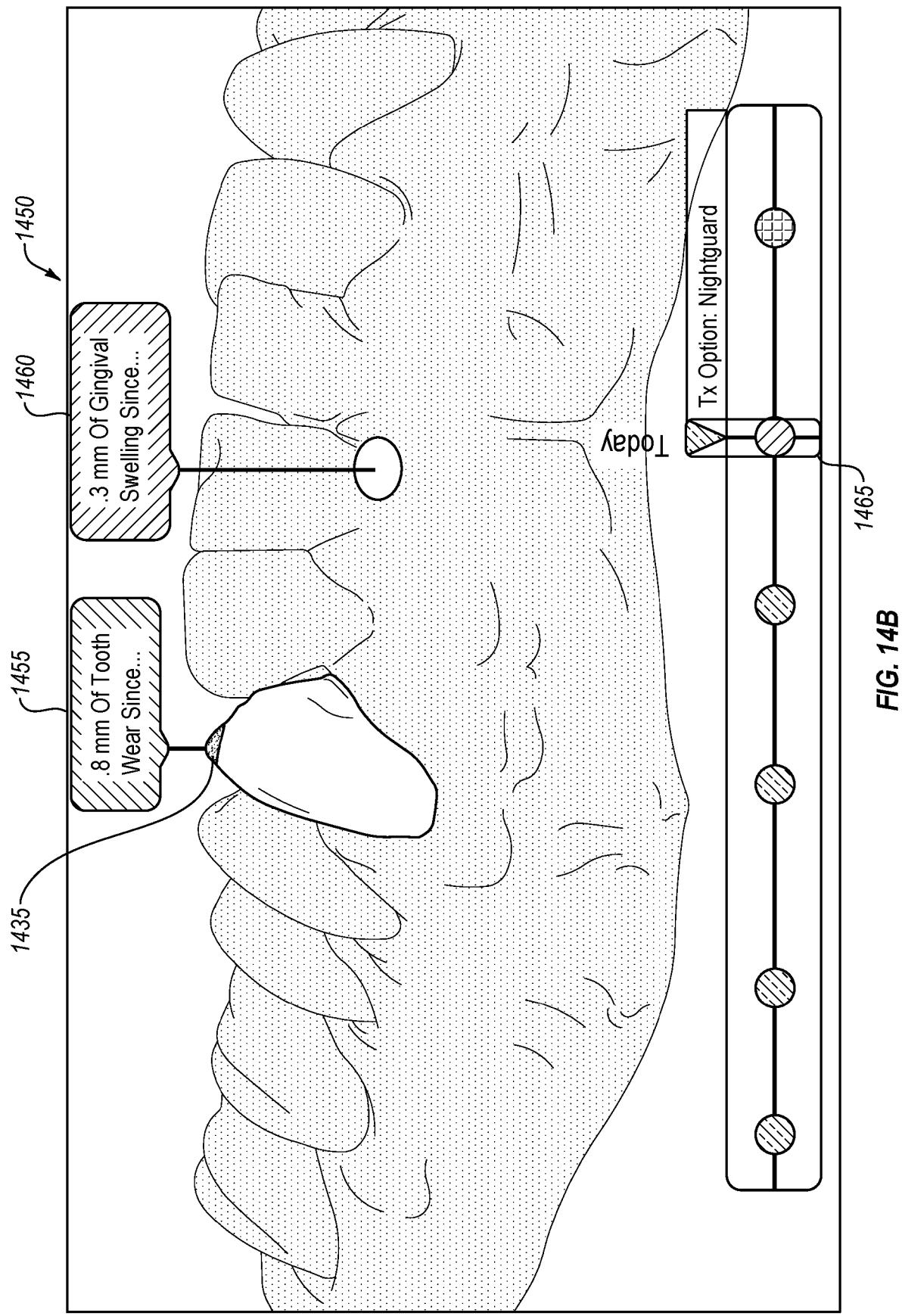
FIG. 14B illustrates a representation of a dental arch showing changes that have occurred to the dental arch over time, in accordance with an embodiment.

FIG. 14B illustrates a representation 1450 of a dental arch showing changes that have occurred to the dental arch over time, in accordance with an embodiment. FIB. 14B shows the representation of the dental arch 1415 of FIG. 14A, along with additional information. As shown, in addition to showing the highlighted or accentuated region 1435 that identifies an amount of the tooth that has been worn away between the first scan 1405 and the second scan 1410, the representation 1450 also includes flag 1455 that points to the accentuated region 1435 and an additional flag 1460 that points to a region of gum swelling. Additionally, the representation 1450 is shown with a timeline that shows various past amounts of wear for the tooth and a predicted future amount of wear for the tooth. The timeline also includes a suggested treatment option of a night guard to reduce tooth wear.

Referring back to FIG. 1B, first image data 162 and second image data 163 may include bite information such as an occlusion surface. Occlusion refers to the contact between teeth. More particularly, occlusion is the relationship between the maxillary (upper) teeth and the mandibular (lower) teeth, such as during chewing. A malocclusion is the misalignment of the teeth and/or jaw that impairs a person's bite. Contacts between maxillary teeth and mandibular teeth may be divided into functional contacts and interfering contacts. The first image data 162 and/or second image data may include an occlusion map that shows functional contacts and interfering contacts. These functional contacts and/or interfering contacts may change over time. For example, a patient may develop further interfering contacts over time. This change in occlusion may be a change of clinical significance that is determined using the techniques set forth above.

Display module 118 may output the representations and/or visual overlays generated by other modules for display to a user.

In addition to spatial changes in the dental arch such as tooth movement, gum recession, tooth wear, tooth occlusion, and gum swelling, appearance changes can also be clinically significant. For example, a change in color of a tooth or tooth region can point to various problems, such as development of a lesion or dental caries. For example, a dark spot or a white spot may indicate a problem area in a tooth. A lesion can start as a very small color change, and grow to a larger dot, before penetrating into inner layers of a tooth. However, some tooth stains may look like lesions. Comparing appearance of the dental arch over time (in a longitudinal study) can help early detection of lesions and caries with reduced false alarms.

In one embodiment, dental issue identifier 115 additionally includes an appearance comparator 172. Appearance comparator 172 determines difference in appearance (e.g., not based on changes in shape or physical position) between the third representation or additional representation that is output by spatial comparator 168, image difference separator 178 and/or representation generator 179 and a first representation from the first image data 162. Alternatively, appearance comparator 172 may compare a first representation of the dental arch from the first image data 162 to a second representation of the dental arch from the second image data 163 to determine appearance differences. As used herein, appearance includes color, hue, intensity, purity (whiteness), speculator or diffusion, percolation, transparency or translucency, and/or other visual indicators. Appearance may also include fluorescence level, which may be determined by shining a short wavelength light into a tooth and receiving a longer wavelength light that is then emitted by the tooth. For example, a blue light may be emitted and blue to green light may be received, red light may be emitted and red to near infrared light may be received, or ultraviolet light may be emitted and ultraviolet to visible light may be received. Appearance differences are detected by comparing a generated representation to which rigid and non-rigid transformations have been applied to the first representation from the first image data 162 to identify differences in appearances between regions of the dental arch at a first time and the same regions of the dental arch at a second time.

Each point of the dental arch from one representation is compared to the same point in the additional representation of the dental arch. Once the point and/or surface correspondence is complete, appearance comparator 172 can subtract the color values (or other appearance values) of the reference surface from those of the test surface. The differences can be shown as a difference map generated by representation generator 179.

In some instances, scanners may introduce scanner inaccuracy to the appearance, such as color changes from scan to scan. Accordingly, in one embodiment appearance comparator 172 performs a color calibration to eliminate non-clinical appearance differences that are attributable to scanner inaccuracy or differences in scanners. The color calibration may correct for changes of illumination with distance, changes of illumination with angle and changes within the FOV of the scanner. Scanning differences are primarily caused by distance and angle of image capture. To overcome scanning differences, appearance comparator 172 may use a predefined or learned reference model to estimate parameters in a small region. Alternatively, appearance comparator 172 may apply a model that takes into account stray light, self-illumination and percolation effects of a generated image.

After either technique of eliminating color differences due to scanner inaccuracy is applied, some residual color and other appearance differences will remain. A few techniques may be used to remove such residual differences, either alone or in combination. One such technique is to apply a low pass filter on the three dimensional color map generated based on the appearance comparison between the representations of the dental arch. The low pass filter may separate out low frequency changes (e.g., with a spatial frequency of 10 mm and less) that may be due to scanner inaccuracies.

Another technique of eliminating color differences due to scanner inaccuracy is to determine a smooth function that when applied to one representation will cause that representation to have the appearance of the other representation. To learn the smooth function, appearance comparator 172 may take all matching points in an area, and perform a mean square error (MSE) estimate or L1 estimate to a function to bring all points as near as possible to the other points. For example, the following functions may be solved for:

$$R_1 = f(R_2, G_2, B_2, x, y)$$

$$G_1 = f(R_2, G_2, B_2, x, y)$$

$$B_1 = f(R_2, G_2, B_2, x, y)$$

Where x and y are the coordinates of a point on the dental arch, $R_1$, $G_1$ and $B_1$ are the color values of a point (x,y) in the first representation, and $R_2$, $G_2$ and $B_2$ are the color values of the point in the second representation. A polynomial function (e.g., a second degree or third degree polynomial function) may also be used as the smoothing function. Once the smoothing function is generated, it may be applied to a color map of one representation of the dental arch to cause it to have colors that more closely align to colors of the second representation.

Another technique of eliminating color differences due to scanner inaccuracy is to normalize the surface appearance of points in each representation to local environments for those points. For this technique, appearance comparator 172 identifies a tooth or point neighboring region, and builds a normalized map. A region which is identical to its neighbor will have a zero value in the normalized map. A normalized map may be generated for each representation, and the two normalized maps may be compared rather than the raw color maps of the two representations.

Another technique of eliminating color differences due to scanner inaccuracy is to generate color models of each representation, and then generate additional maps that are based on derivatives of the color maps. These maps of the derivatives can then be compared to identify changes in appearance between the two representations. This may remove slow change colors that may be an error introduced by scanners.

Remaining appearance differences may be accentuated in the same manner as described above with reference to spatial differences. For example, a color overlay may be generated, flags may be used, appearance differences may be extrapolated into the future, and so on. In an example, a border or contour of a region that experiences a color change may be added to a visual overlay to call attention to the appearance change.

FIGS. 2-3B, 6, 8 and 10 below describe example applications of determining dental issues of a patient based on comparison of image data taken at different times. The examples are described with reference to flow charts describing processes of determining dental issues. The flow charts provide example processes that may be performed by system 100 of FIG. 1A and/or by other computing devices. The methods depicted in FIGS. 2-3B, 6, 8 and 10 may be performed by a processing logic that may comprise hardware (e.g., circuitry, dedicated logic, programmable logic, microcode, etc.), software (e.g., instructions run on a processing device to perform hardware simulation), or a combination thereof.

Figure 2:
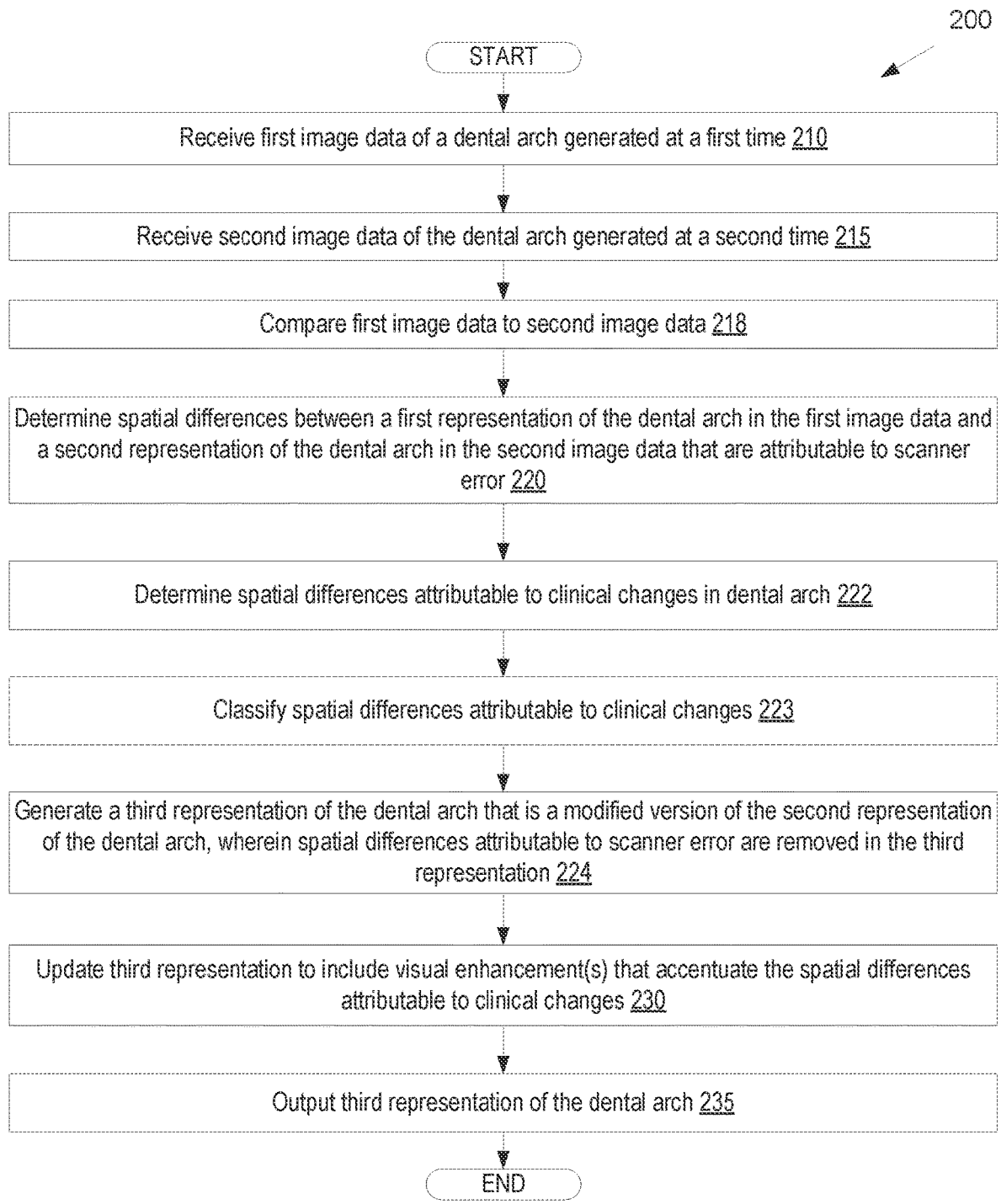
FIG. 2 illustrates a flow diagram for a method of identifying dental issues, in accordance with an embodiment.

FIG. 2 illustrates a flow diagram for a method 200 of identifying dental issues, in accordance with an embodiment. At block 210 of method 200, processing logic receives first image data of a dental arch generated at a first time. The first image data may be a first three-dimensional representation of the dental arch that was generated based on an intraoral scan taken at the first time. At block 215, processing logic receives second image data of the dental arch generated at a second time. The second image data may be a second three-dimensional representation of the dental arch that was generated based on an intraoral scan taken at the second time.

At block 218, processing logic compares the first image data to the second image data. This may include comparing the first three-dimensional representation from the first image data to the second three-dimensional representation from the second image data and registering the first representation to the second representation as discussed above with reference to FIG. 1B. Given two surfaces (e.g., the first three-dimensional representation and the second three-dimensional representation of the dental arch), one of them being a test surface and the other being a reference surface, processing logic determines the differences between the test surface and the reference surface. Any of the aforementioned techniques for comparing the first representation (e.g., reference surface) to the second representation (e.g., test surface) described above may be applied. For example, techniques such as surface overlay and coloring of a test surface according to distance from points on the test surface to nearest points on the reference surface may be used. Both approaches depend on a fine alignment of the test surface to the reference surface that is typically achieved by semi-automatic algorithms because for significantly mismatching surfaces different alignment options are possible and it is difficult to fully automate the alignment process. One reason for this difficulty is that standard image registration methods do not handle situations where there are several kinds of differences between surfaces of a significantly various scale. Accordingly, standard image alignment and image registration methods are not generally applicable for comparison between 3D representations of a dental arch generated by an intraoral scanner. However, in embodiments described herein the alignment and image registration process is fully automated and accommodates the multiple different scales of differences between representations of the dental arch.

At block 220, processing logic determines spatial differences between the first representation and the second representation that are attributable to scanner inaccuracy. At block 222, processing logic determines spatial differences attributable to clinical changes in the dental arch. Spatial differences attributable to scanner inaccuracy and spatial differences attributable to clinical changes may each be identified based on a scale (e.g., spatial frequency) of the changes. Spatial differences having a large scale (and thus a low spatial frequency) such as differences in arch length and jaw width may be identified as global differences that are caused by scanner inaccuracy. Changes in arch width have a scale (and spatial frequency) of about 5-10 cm and a magnitude of about 0.5-5.0 mm. Spatial differences having smaller scale (and thus a higher spatial frequency) such as differences in tooth movement, tooth wear, gum recession, and gum swelling may be identified as local differences that are caused by clinical changes to the dental arch. Changes in teeth position have a scale (and spatial frequency) of about 1-2 cm and a magnitude of about 0.3-5.0 mm. Changes in gingiva or gum recession and inflammation have a scale (and spatial frequency) of about 1-5 mm and a magnitude of about 0.2-0.3 mm. Changes in tooth wear and changes in tooth shape due to restorations (e.g., crowns, fillings, etc.) have a scale (and spatial frequency) of about 0.2-1.0 mm and a magnitude of about 0.03-0.3 mm. With traditional comparison visualization methods, large-scale changes such as teeth movements or jaw expansion nearly completely hide smaller changes such as tooth wear. However, the multilevel approach to surface matching and image registration performed by processing logic enables the separation of differences between surfaces into several levels, and further enables the visualization of changes of different scales separately. Such separation can be achieved because changes such as tooth wear are strongly localized and thereby can be separated from larger, smoother, lower frequency changes such as teeth movement or arch expansion. An additional benefit is that processing logic may perform image registration and determine surface differences in a completely automatic fashion that does not require manual intervention by a user in the surface alignment process.

At block 223, processing logic may classify the spatial differences attributable to clinical changes. For example, processing logic may determine the scale or spatial frequency for each of the determined differences, and classify those differences as one of changes in teeth position, changes in the gingiva (e.g., gum recession or gum inflammation), changes in tooth shape (e.g., tooth wear and restorations), and so on based on the scale or spatial frequency. Spatial differences may additionally or alternatively be classified using one or more specific dental classification rules or algorithms. For example, a first classification rule may identify changes to the gingiva, a second classification rule may determine changes to tooth shape, a third classification rule may determine tooth movements, and so on.

At block 224, processing logic generates a third representation of the dental arch that is a modified version of the second representation of the dental arch. Spatial differences attributable to scanner inaccuracy may be removed in the third representation. Accordingly, the remaining spatial differences are those that are attributable to clinical change in the dental arch. At block 230, processing logic updates the third representation to include visual enhancements that accentuate the spatial differences attributable to clinical changes. This may include generating a visual overlay such as a color overlay and or extrapolating the spatial differences into the future. At block 235, processing logic outputs the third representation of the dental arch. For example, processing logic may display the third representation of the dental arch for view by a dental practitioner or patient.

Figure 3A:
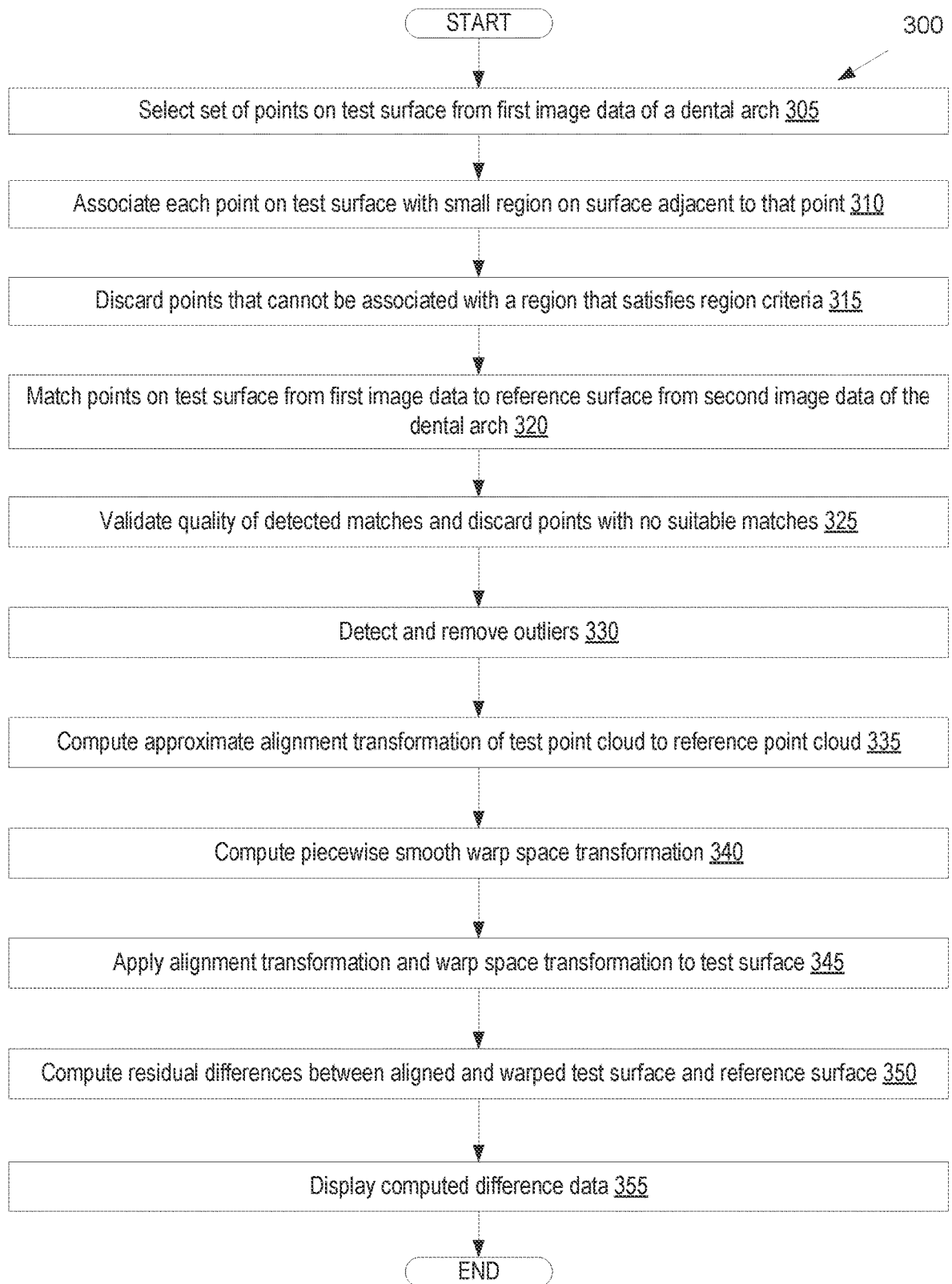
FIG. 3A illustrates a flow diagram for a method of registering image data of a dental arch and identifying and classifying dental issues, in accordance with an embodiment.
Figure 4A:
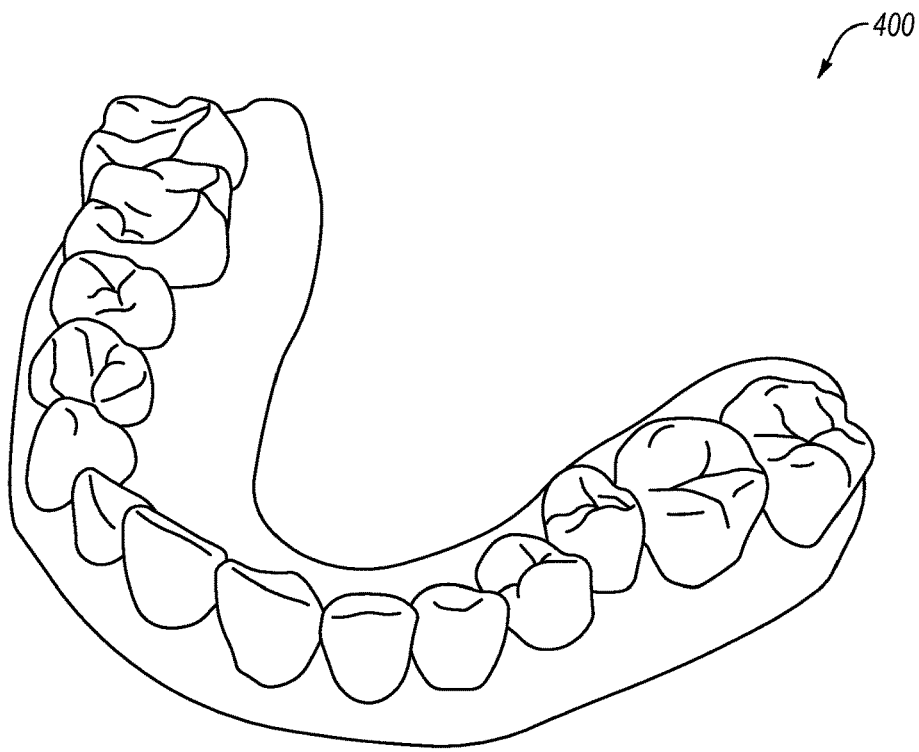
FIG. 4A is a diagram illustrating first image data for a dental arch, in accordance with an embodiment.
Figure 4B:
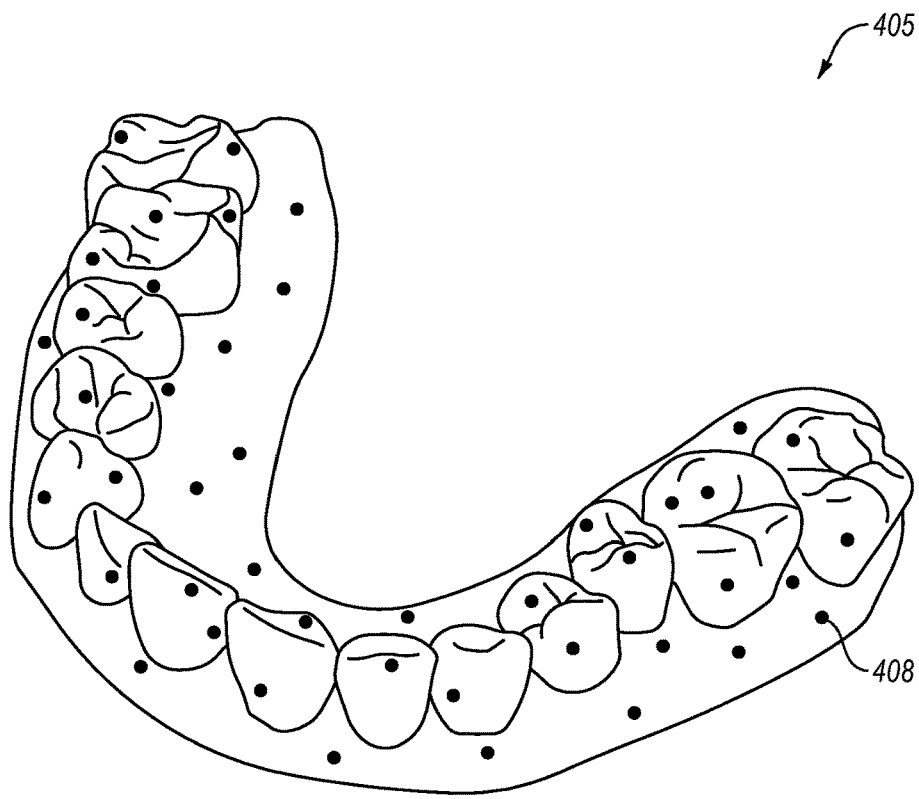
FIG. 4B is a diagram illustrating the dental arch of FIG. 4A after points on a surface of the dental arch are selected, in accordance with an embodiment.

FIG. 3A illustrates a flow diagram for a method 300 of registering image data of a dental arch (e.g., performing image alignment) and identifying and classifying dental issues, in accordance with an embodiment. At block 305 of method 300, processing logic selects a set of points on a test surface from the first image data of the dental arch. The test surface may be a surface of a first three-dimensional representation of the dental arch generated based on a first intraoral scan. Suitable methods for selecting the set of points include random sampling of surface vertices, binning of vertices to a voxel grid and averaging in each voxel of the voxel grid, and feature detection (e.g., such as teeth cusp detection). FIG. 4A is a diagram illustrating first image data for the dental arch that shows the test surface 400 of the 3D representation of the dental arch. FIG. 4B is a diagram illustrating the test surface 405 of the dental arch of FIG. 4A after points 408 on the test surface are selected, in accordance with an embodiment.

Figure 4C:
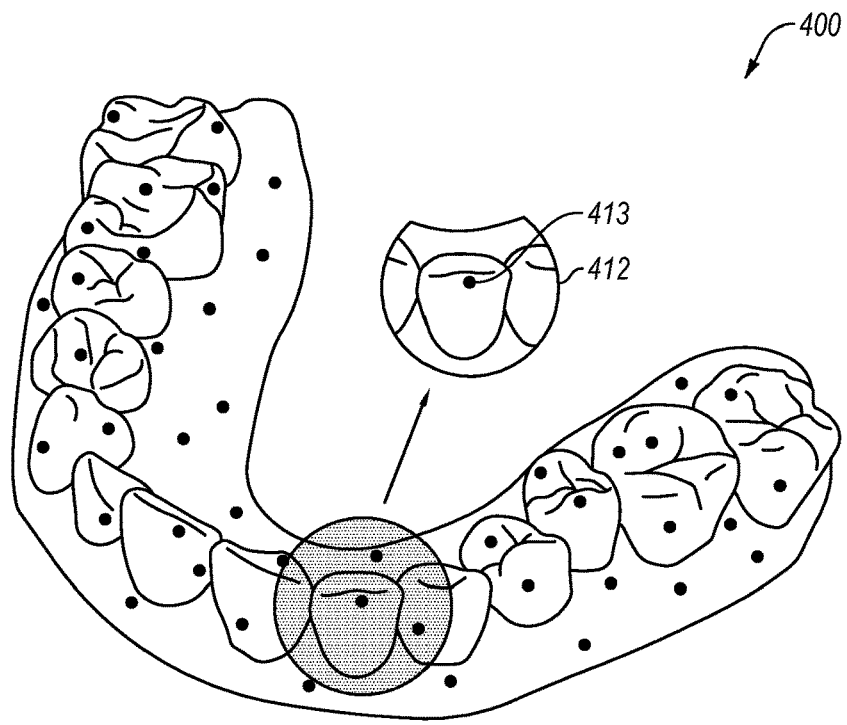
FIG. 4C is a diagram illustrating the dental arch of FIG. 4B showing a particular region around a selected point on the surface, in accordance with an embodiment.

Returning to FIG. 3A, at block 310 processing logic associates each point on the test surface with a small region on the test surface adjacent to that point. One possible suitable method that may be used for selecting these small regions (referred to as surface patches) is to select parts of the surface that are less than a threshold distance away from a selected point, and keeping a connected surface patch that contains the point itself. Another suitable technique is to perform tooth segmentation and associate each point with a tooth crown that includes the selected point or a part of such tooth crown. FIG. 4C is a diagram illustrating the test surface 410 of the dental arch of FIG. 4B showing a particular region or surface patch 412 around a selected point 413 on the test surface 410, in accordance with an embodiment.

Returning to FIG. 3A, at block 315 processing logic discards points that cannot be associated with a region that satisfies one or more region criteria. For example, points that cannot be associated with a sufficiently good region of a surface are discarded. A first region criterion may be a surface patch size threshold. Points that cannot be associated with a surface patch having at least a minimum size may not satisfy the surface patch size threshold a second region criterion and may be discarded. A second region criterion may be a dental feature criterion. Points that cannot be associated with a tooth crown, for example, may fail to satisfy the dental feature criteria and may be discarded.

Figure 4D:
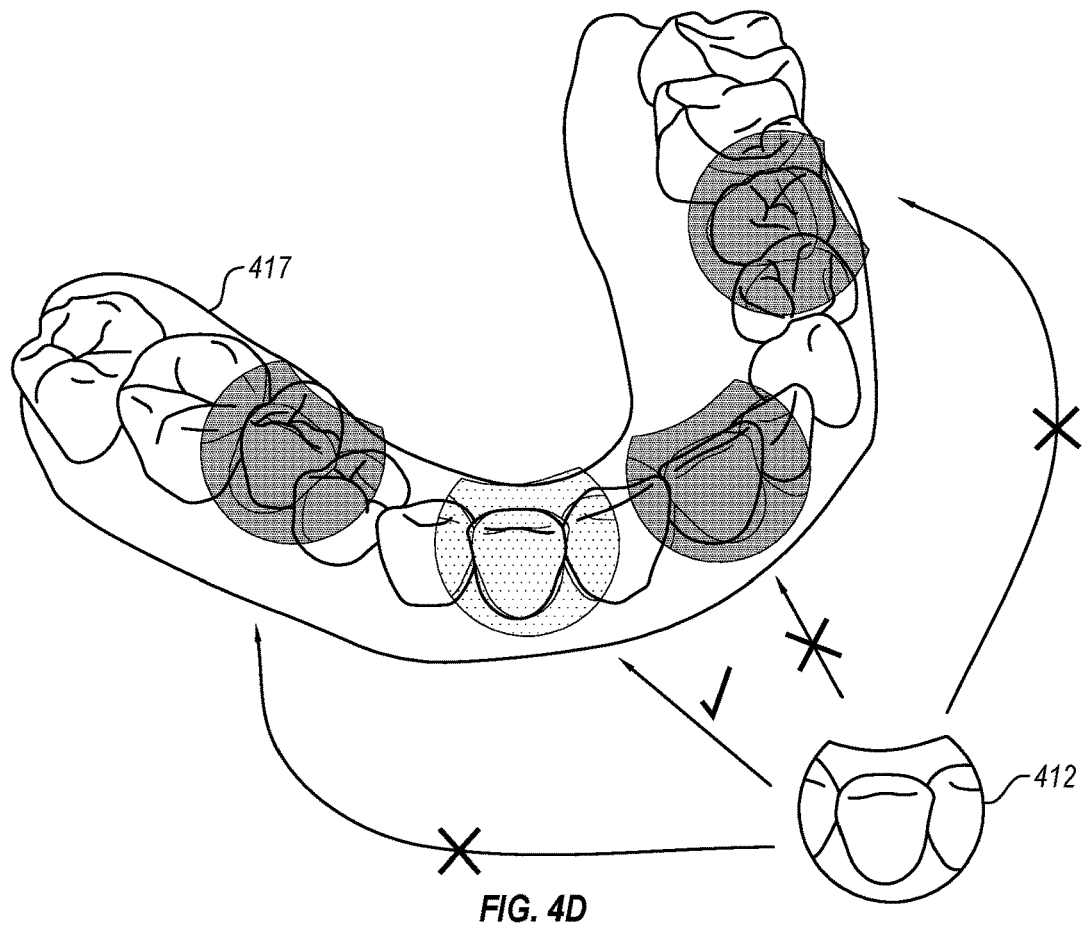
FIG. 4D is a diagram illustrating matching of the particular region of FIG. 4C to second image data for the dental arch, in accordance with an embodiment.

At block 320, processing logic matches points on the test surface from the representation of the dental arch in the first image data to a reference surface from the representation of the dental arch in the second image data. One matching technique that may be used includes running an iterative closest point (ICP) algorithm from several staring positions. Another matching technique includes detecting a number of orientation-independent surface features on test surfaces of one image and reference surfaces on the other image. For each feature on a test surface, processing logic may find all similar features on the reference surface and vote for particular transforms that would align features on the test surface with the features on the reference surface. The transformation with the most votes may then be picked, and a result may be refined using an ICP algorithm. FIG. 4D is a diagram illustrating matching of the particular region or surface patch 412 of FIG. 4C to a reference surface 417 from the second image data for the dental arch, in accordance with an embodiment.

Returning to FIG. 3A, at block 325 processing logic validates the quality of detected matches with a suitable method and discards points that did not match well. One suitable method for validation includes computing a percentage of surface area on a tested part of the test surface that is less than a threshold distance (e.g., in millimeters) away from the reference surface after alignment. A match may be validated if the size of the surface area that matched is larger than a size threshold. Another suitable method for validation includes computing an average or median distance between vertices of a tested part of the test surface and the reference surface after alignment. If the average or median between vertices is less than a threshold distance, then validation may be successful.

At block 330, processing logic computes a mean and/or median alignment of the entire set of matches. Processing logic may detect and remove outliers that suggest variants of alignment of the test surface and reference surface that are too different from the mean or median alignment of the entire set of matches by using an appropriate method. For example, surface patches for which the alignment of the test surface to the reference surface has an alignment value that differs from the mean or median by more than a threshold may be too different. One appropriate method that may be used is the random sample consensus (RANSAC) algorithm. If two surfaces are not comparable, then processing logic will determine that the registration has failed based the number of surviving points would be too small to reasonably cover the entire test surface. This might happen, for example, if input data contained a mistake (e.g., a user tried to match an intraoral scan of one person to an intraoral scan of another person). Processing logic may check for such a condition and report an error if this occurs.

A result of the surface matching may be a dense set of pairs of matching points, with each pair corresponding to a region on the test surface and a matching region on the reference surface. Each such region is also associated with a point, so each pair can also be viewed as a pair of a point on the test surface and a matching point on reference surface. An ordered set of these points on a test surface is a point cloud on the test surface, and a set of matching points on a reference surface ordered in the same way is a matching point cloud on the reference surface.

Figure 4E:
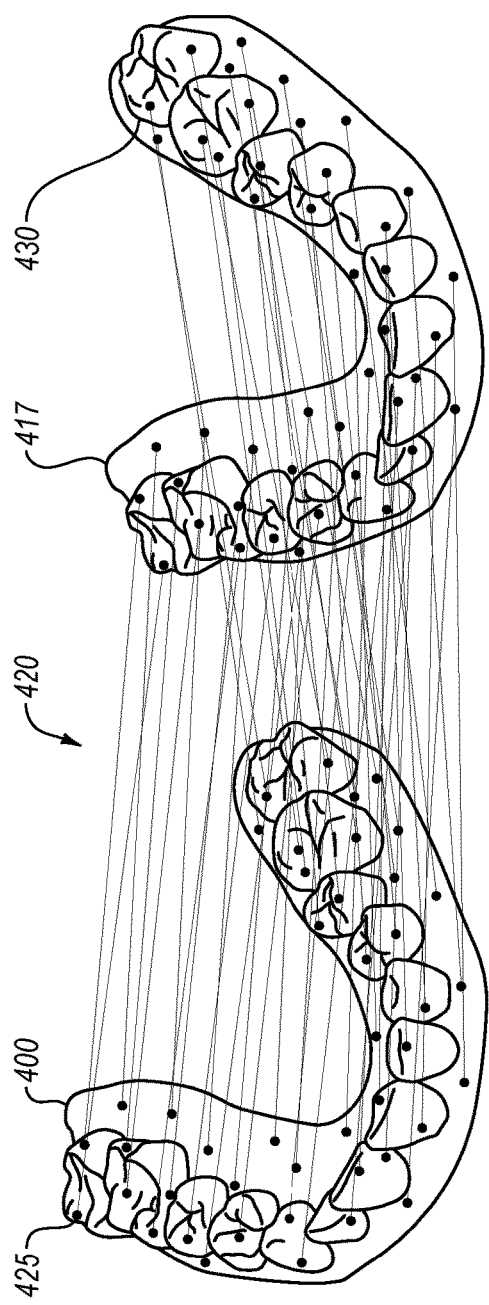
FIG. 4E illustrates a mapping of points on a test surface to corresponding points on a reference surface.

At block 335, processing logic computes an approximate alignment transformation to align a test point cloud for the test surface to a reference point cloud for the reference surface. One example of a suitable algorithm for computing the alignment transformation is the least-squares minimization of distance between the test and reference point clouds. The approximate alignment transformation may be a rigid alignment transformation. After approximate alignment via a rigid transformation of the test surface, test and reference point clouds won't coincide exactly. FIG. 4E illustrates a mapping 420 of points 425 on the test surface 400 to corresponding points 430 on the reference surface 417.

Figure 4F:
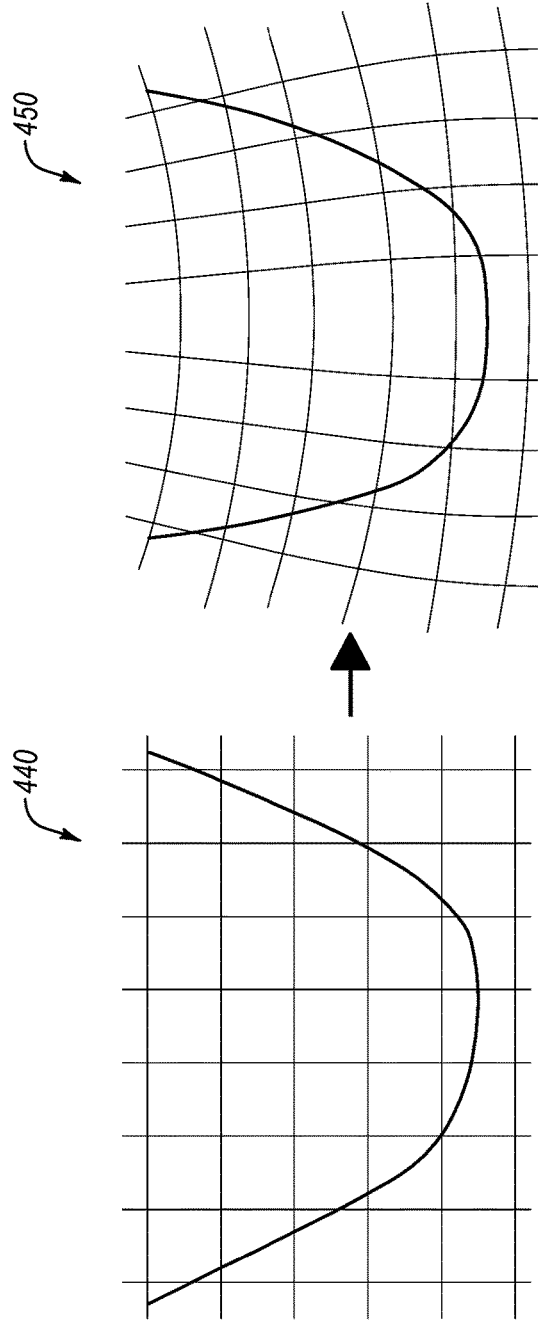
FIG. 4F is a diagram illustrating a warp space transformation between first image data of a dental arch and second image data of the dental arch, in accordance with an embodiment.

At block 340, processing logic computes a non-rigid transformation such as a piecewise-smooth warp space transformation that smoothly deforms a 3D space of the test surface such that 1) this deformation is as smooth as possible and b) the test point cloud after application of the warp transformation is much better aligned with a reference point cloud. Possible implementation options include, but are not limited to, radial basis function interpolation, thin-plate splines (TPS) and estimating teeth movements and propagating them to a nearby space. FIG. 4F is a diagram illustrating a warp space transformation between first image data (test surface) 440 of a dental arch and second image data (reference surface) 450 of the dental arch, in accordance with an embodiment. A magnitude of the warp space transformation may be identified as a global component of spatial differences that are attributable to scanner inaccuracy. Accordingly, the warp space transformation may identify the spatial differences caused by scanner inaccuracy.

Once corresponding point sets are determined between surface patches of the two images, determination of the transformation between the two sets of corresponding points in two coordinate frames can be solved. Essentially, an image registration algorithm may compute a transformation between two images that will minimize the distances between points on one surface, and the closest points to them found in the interpolated region on the other image surface can be used as a reference. The transformation may include rotations and/or translational movement in up to six degrees of freedom. Additionally, the transformation may include deformation of one or both of the images (e.g., warp space transformations and/or other non-rigid transformations). A result of the image registration may be one or more transformation matrix that indicates the rotations, translations and/or deformations that will cause the one image to correspond to the other image.

At block 345, processing logic applies an alignment transformation and a non-rigid (e.g., warp space) transformation to the test surface. At block 350, processing logic computes residual differences between the aligned and warped test surface and the reference surface. This residual may be reported as a "local" component of the surface difference that is attributable to clinical changes in the dental arch. A possible implementation option includes computing a distance to a nearest point of the reference surface for each point of an aligned and warped test surface and then coloring the test surface accordingly (e.g., coloring based on a magnitude of the distance, where a first color may be used for a first distance magnitude, a second color may be used for a second distance magnitude, and so on). Another possible implementation option includes performing an additional comparison as set forth above to split the remaining differences into additional levels (e.g., into tooth movement, changes in gingival shape, changes to the tooth surface, and so on). For example, the operations of blocks 305-345 may be repeated. In a first repetition of the operations of blocks 305-345, the test surface that may be used is the aligned and warped test surface (in which the spatial differences caused by scanner inaccuracy have been removed). As a result, spatial differences caused by tooth movement may be the spatial differences with the largest scale or spatial frequency that remain. An additional warp space transformation may show the spatial differences caused by tooth movement. In a second repetition of the operations of blocks 305-345, the spatial differences with the next largest scale or spatial frequency may be identified, and so on.

At block 355, processing logic generates a representation of the dental arch that shows some or all of the differences between the test surface and the reference surface. In one embodiment, alignment transformation (e.g., transformation in position and/or orientation) and warp space transformation (e.g., deformation) computed from a point cloud may be applied to the entire test surface. A magnitude of the warp space transformation may be reported as a "global" component of a surface difference and visualized with a suitable method. The differences caused by scanner inaccuracy as represented in the warp space transformation may be visualized using a suitable method. Suitable methods include a per-point coloring of the test surface according to a magnitude of the warp movement at this point and coloring of an entire tooth crown according to a magnitude of its movement. Such global component of the surface difference may be the surface difference that is attributable to scanner inaccuracy. Similar visualization techniques can be used for each of the different levels. Multiple levels of spatial differences may be shown together (e.g., each with different coloring or other different visualization. Alternatively, a user may turn on or off visualization of one or more of the levels. The visualization may highlight or accentuate regions of significant changes. Additionally, the differences may be filtered to hide insignificant changes and simplify analysis. In one embodiment, a dental practitioner may specify thresholds of importance for each type of clinical change. For example, a dental practitioner may specify a single threshold or a lower and upper threshold for changes in the gingival line, for tooth movement, for tooth wear, and so on. A filter may be used to filter out those changes that have a smaller magnitude than a lower threshold and/or to emphasize those changes that have a higher magnitude than the upper threshold. Default thresholds may also be used. In one example, spatial differences having a magnitude that is less than a lower threshold may be shown with a first color, spatial differences having a magnitude between the lower and upper thresholds may be shown with a second color, and spatial differences having a magnitude that is greater than the upper threshold may be shown with a third color.

Figure 3B:
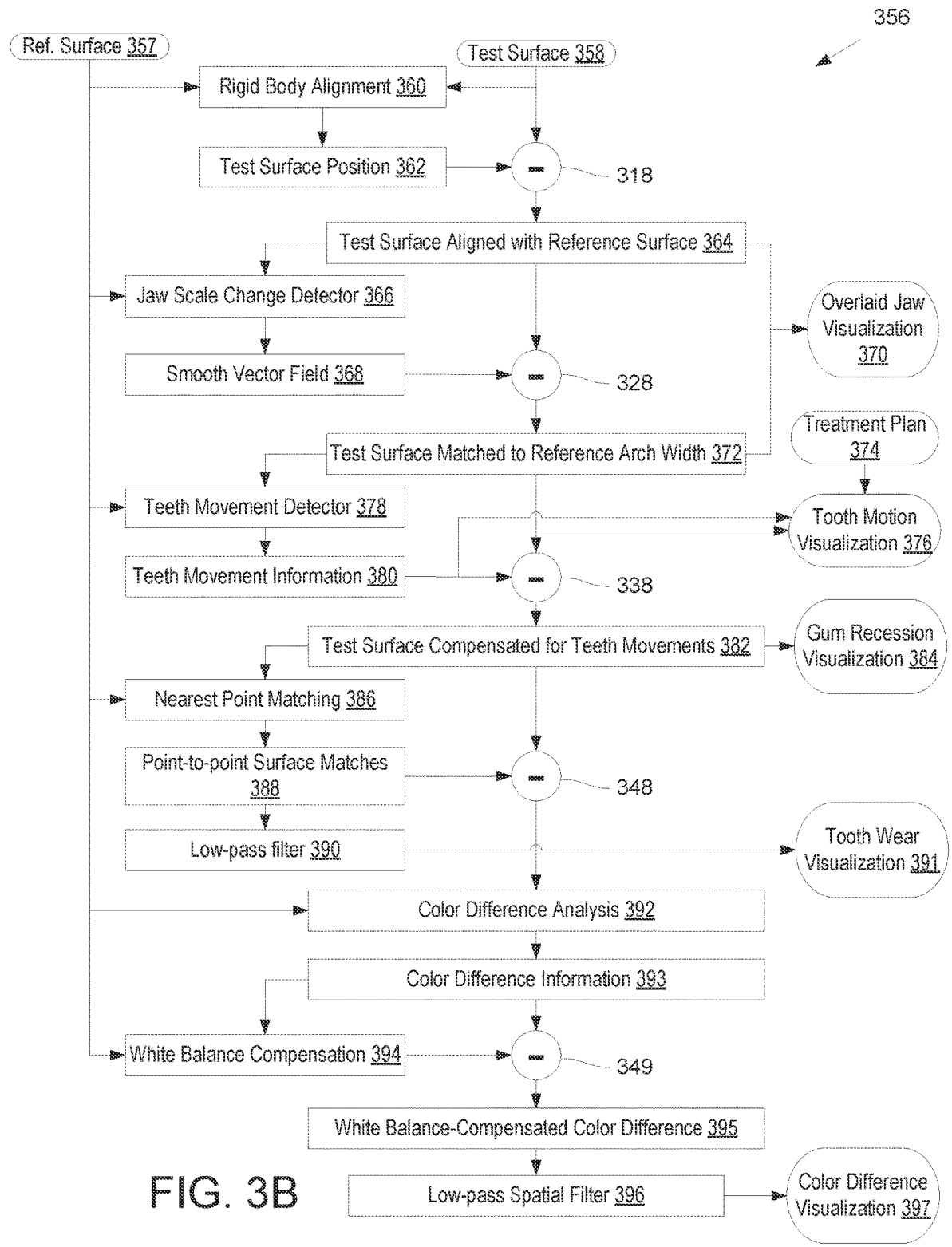
FIG. 3B illustrates a flow diagram for a method of registering image data of a dental arch and identifying and visualizing dental issues, in accordance with an embodiment.

FIG. 3B illustrates a flow diagram for a method 356 of comparing image data of a dental arch and identifying and visualizing dental issues, in accordance with an embodiment. The method 356 begins with receiving a reference surface (first image data of a dental arch) 357 and receiving a test surface 358 (second image data of the dental arch). Method 356 is described with reference to making modifications to the test surface 358 for comparison and matching with the reference surface 357. However, it should be understood that modifications may instead be made to the reference surface 357 for comparison and matching with the test surface 358.

At block 360, a rigid body alignment is determined for alignment of the test surface 358 to the reference surface 357. At block 362, surface positions from the rigid body alignment are tested. At block 318, the test surface is modified using the rigid body transformation. At block 364, the test surface is therefore aligned with the reference surface using the rigid body alignment. A visualization of the alignment may be shown at block 370.

At block 366, a jaw scale change detector is applied to identify large scale differences of changes in the jaw scale (e.g., jaw width) or arch length between the modified test surface and the reference surface. The jaw scale detector may be a first low pass filter. At block 368, a smooth vector field is determined for a non-rigid alignment between the rigidly aligned test surface 358 and reference surface 357. At block 328, the test surface is further modified using the smooth vector field.

At block 372 the test surface 358 is therefore matched to the arch width of the reference surface 357. The overlay of the jaw visualization may then be output at block 370. If an overlay was earlier output, the overlay may be updated.

At block 378, the test surface 358 as modified at block 372 is compared to the reference surface 357 and processed by a teeth movement detector. The teeth movement detector may be another low pass filter having a higher spatial frequency threshold than the first low pass filter. At block 380, teeth movement information is determined based on an output of the teeth movement detector. The teeth movement information, modified test surface and/or a treatment plan 374 may then be used to show a visualization of tooth motion. The treatment plan 374 may indicate planned tooth motion, which may be compared to the actual detected tooth motion. Differences between the planned tooth motion and the actual tooth motion may then be shown in the tooth motion visualization at block 376.

At block 338, the teeth movements are subtracted from the modified test surface to further modify the test surface. At block 382, a test surface that has been compensated for teeth movements is then generated. At block 384, a gum recession visualization may be output.

At block 386 the test surface as modified at block 382 may be compared to the reference surface 357 using nearest point matching. At block 388, point-to-point surface matches may be performed between the modified test surface and the reference surface. At block 390, a low pass filter is applied to the surface matches to determine changes attributable to tooth wear. A tooth wear visualization may then be output at block 391.

At block 348, the test surface 358 is further modified using a result of the point-to-point surface matches. At block 392, a color difference analysis is performed between the modified test surface and the reference surface. At block 394, a white balance compensation is determined for the test surface. At block 349, the test surface is further modified by applying the white balance compensation. At block 395, a white balance-compensated color difference is determined between the modified test surface and the reference surface. At block 396, a low pass spatial filter may then be applied, and a color difference visualization may be output at block 397.

Figure 5A:
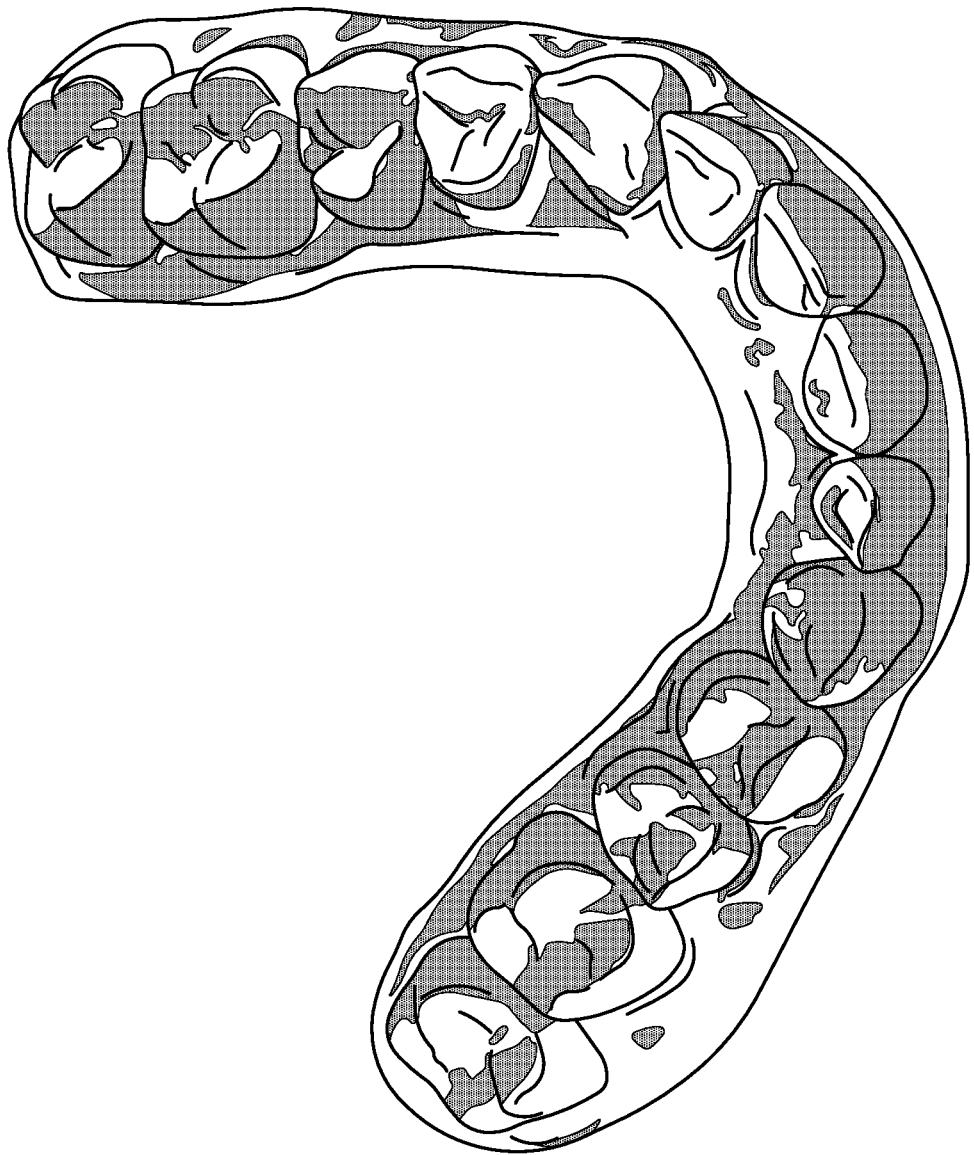
FIGS. 5A-5D illustrate visual maps showing correlation between first image data of a dental arch and second image data of the dental arch, in accordance with an embodiment.
Figure 5B:
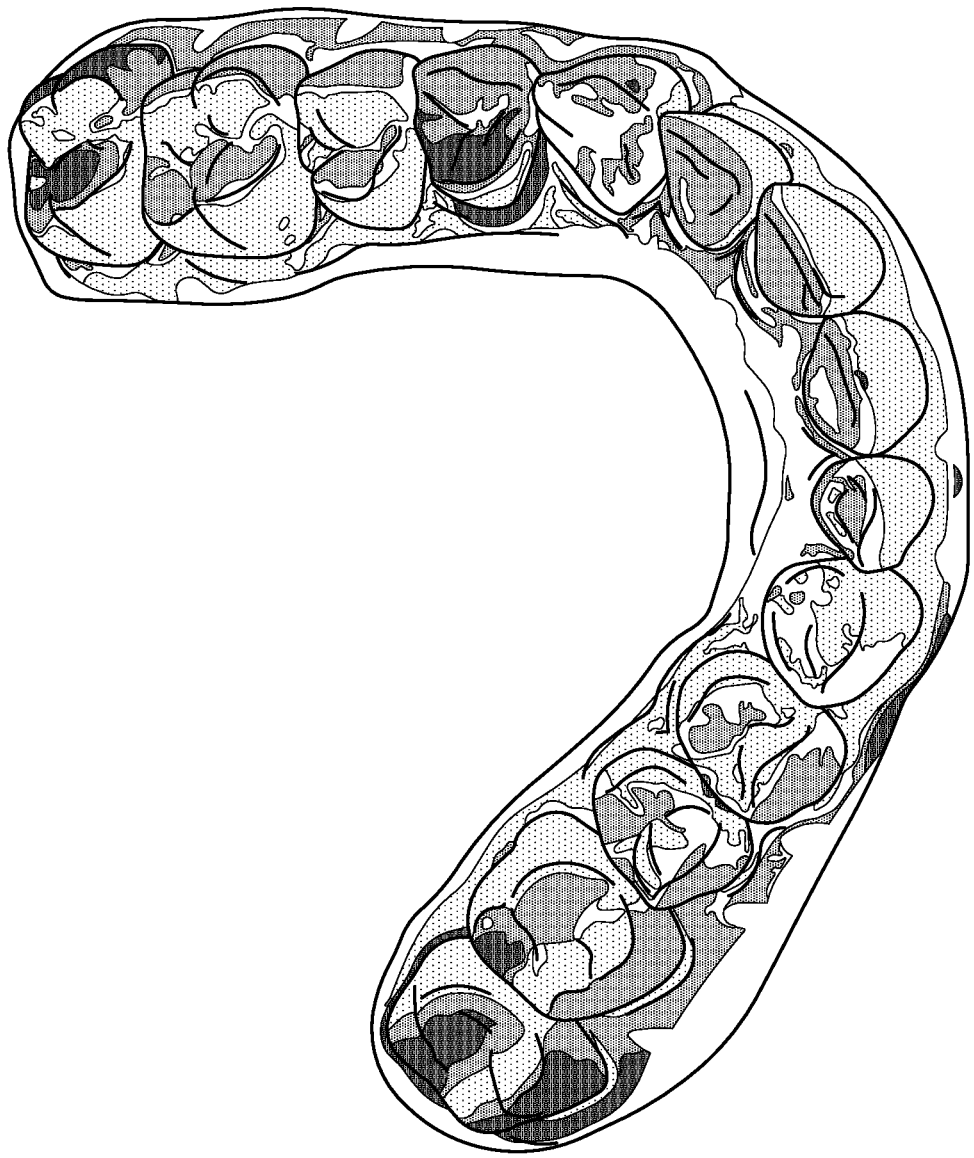
Figure 5C:
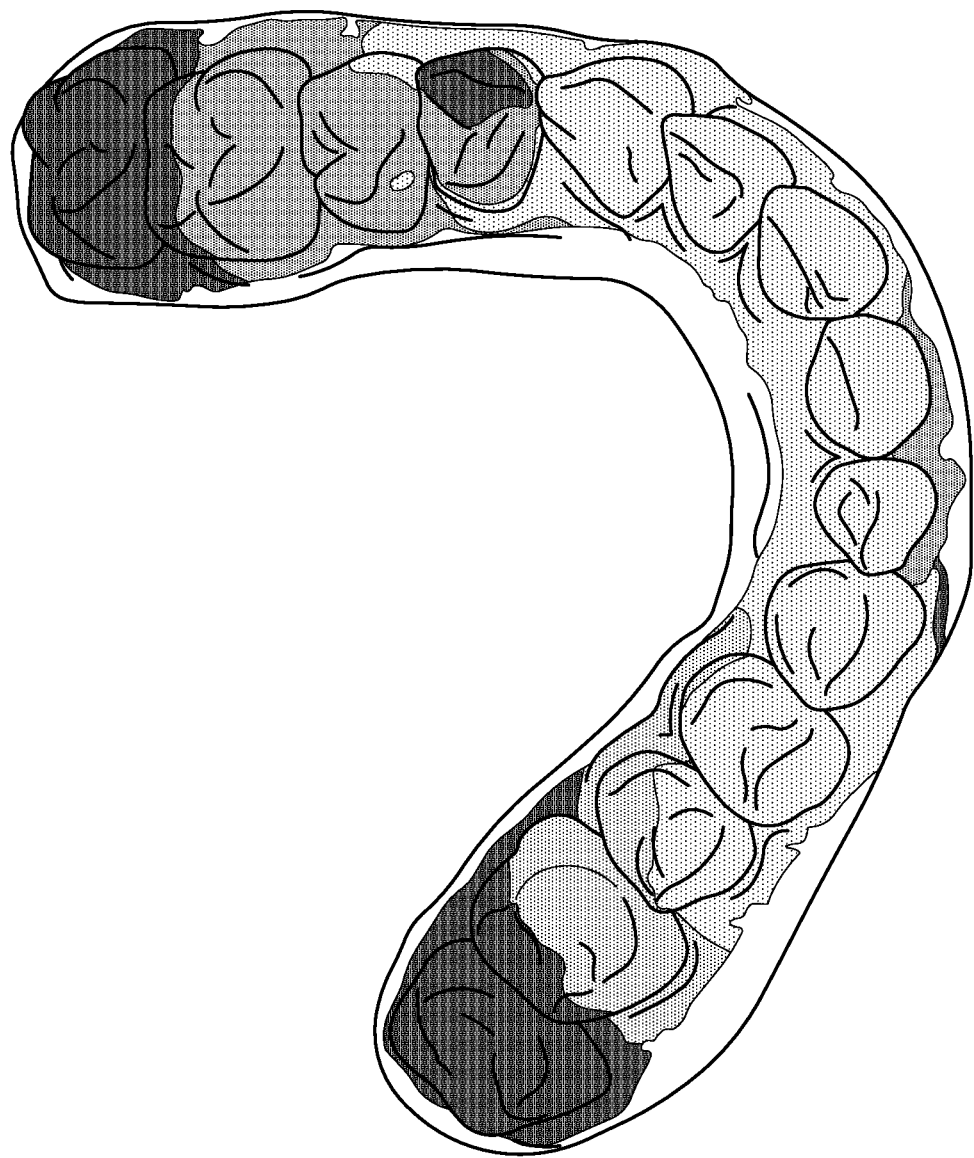
Figure 5D:
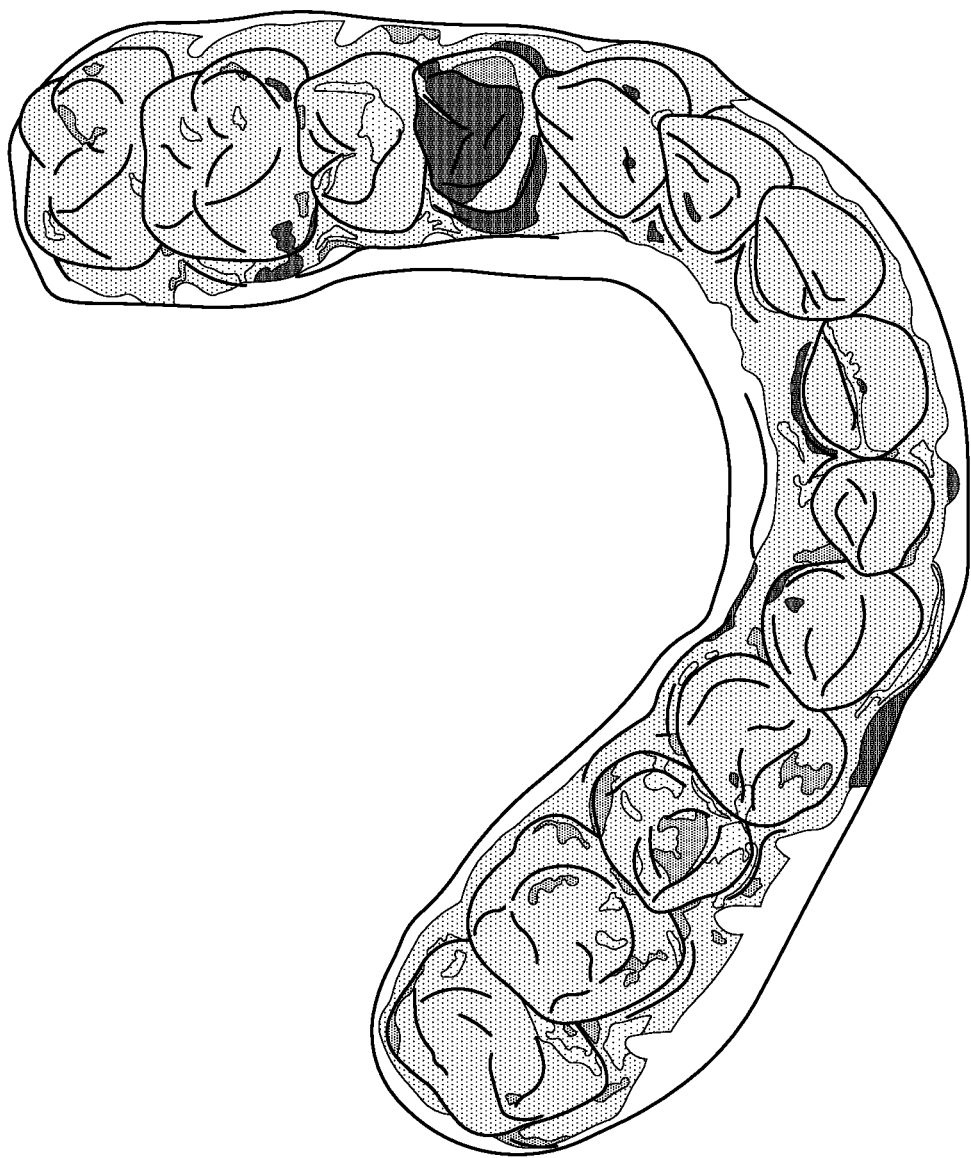

FIGS. 5A-5D illustrate visual maps showing correlation between first image data of a dental arch and second image data of the dental arch, in accordance with an embodiment. In these figures spatial differences have been divided into global and local scales (where each scale represents a different class of spatial difference). FIG. 5A illustrates an overlay between a test and reference surface. FIG. 5B illustrates a traditional point-to-point difference between the test surface and the reference surface with differences appearing on a scale of 20-300 microns. FIG. 5C shows global differences between the test and reference surfaces that are attributable to scanner inaccuracy with differences appearing on a scale of 100-300 microns. FIG. 5D shows local differences between the test and reference surfaces that are attributable to clinical changes on a scale of 20-100 microns. The global differences of FIG. 5C show that the molars have the greatest difference between surfaces. However, the local differences of FIG. 5D show that the fourth tooth in from the right has the most change (e.g., due to grinding tooth moving relative to a neighboring tooth). A dental practitioner looking at any of the visual maps of FIGS. 5A-5C may not easily identify that tooth wear has occurred on the fourth tooth from the right. However, the visual map of FIG. 5D clearly shows to the dental practitioner the clinical changes to this tooth.

Figure 6:
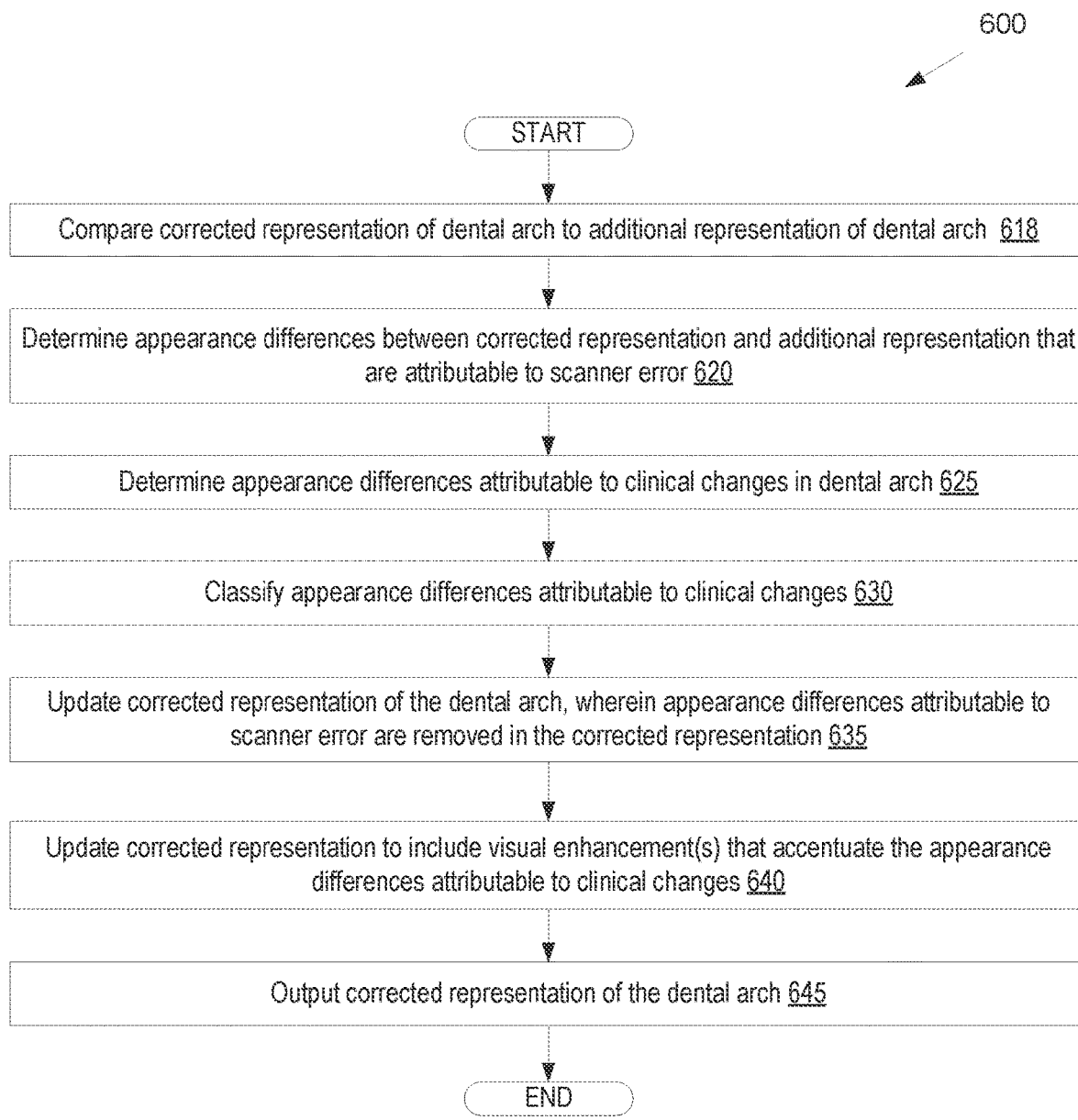
FIG. 6 illustrates a flow diagram for a method of determining appearance differences between first image data of a dental arch and second image data of the dental arch, in accordance with an embodiment.

FIG. 6 illustrates a flow diagram for a method 600 of determining appearance differences between first image data of a dental arch and second image data of the dental arch, in accordance with an embodiment. At block 618 of method 600, processing logic compares a corrected representation of a dental arch to an additional representation of the dental arch. The corrected representation may be a representation that was generated after comparison of a first representation from first image data to a second representation from second image data, where the corrected representation is a modified version of the second representation in which differences between the first and second representations that are attributable to scanner inaccuracy have been removed. For example, the corrected representation may be a representation that is generated after performing the operations of method 200 or method 300. The additional representation may be a representation from first image data of the dental arch, which may have been generated based on a first intraoral scan. At block 620, processing logic determines appearance differences between the corrected representation in the additional representation that are attributable to scanner inaccuracy. At block 625, processing logic determines appearance differences attributable to clinical changes in the dental arch. At block 630, processing logic may classify the appearance differences attributable to clinical changes. Classification may be performed by applying one or more classification rules, where each classification rule may detect a different type of clinical change (e.g., appearance differences in the gums vs. appearance differences in the teeth).

At block 635, processing logic updates the corrected representation of the dental arch. The appearance differences that are attributable to scanner inaccuracy are removed in the corrected representation. At block 640, processing logic updates the corrected representation to include visual enhancements that accentuate the differences that are attributable to clinical changes. At block 645, processing logic outputs the corrected representation of the dental arch.

FIG. 7A illustrates a tooth before a change in appearance of the tooth 700 and a tooth after the change in appearance of the tooth 750. After the change in appearance has occurred, the tooth includes a white area 755 that was not present before the appearance change. Such an appearance change may be detected by method 600.

FIG. 7B illustrates a first representation 760 of a set of teeth and a second representation 770 of the set of teeth. The first representation was generated from image data taken at a first time and the second representation 770 was generated from image data taken at a second time. As shown, an appearance to one of the teeth 765 has changed between the first representation 760 and the second representation 770. Specifically, the translucency of the tooth 765 has increased at a region 775 of the tooth 765. Such an appearance change may be detected by method 600.

Figure 8:
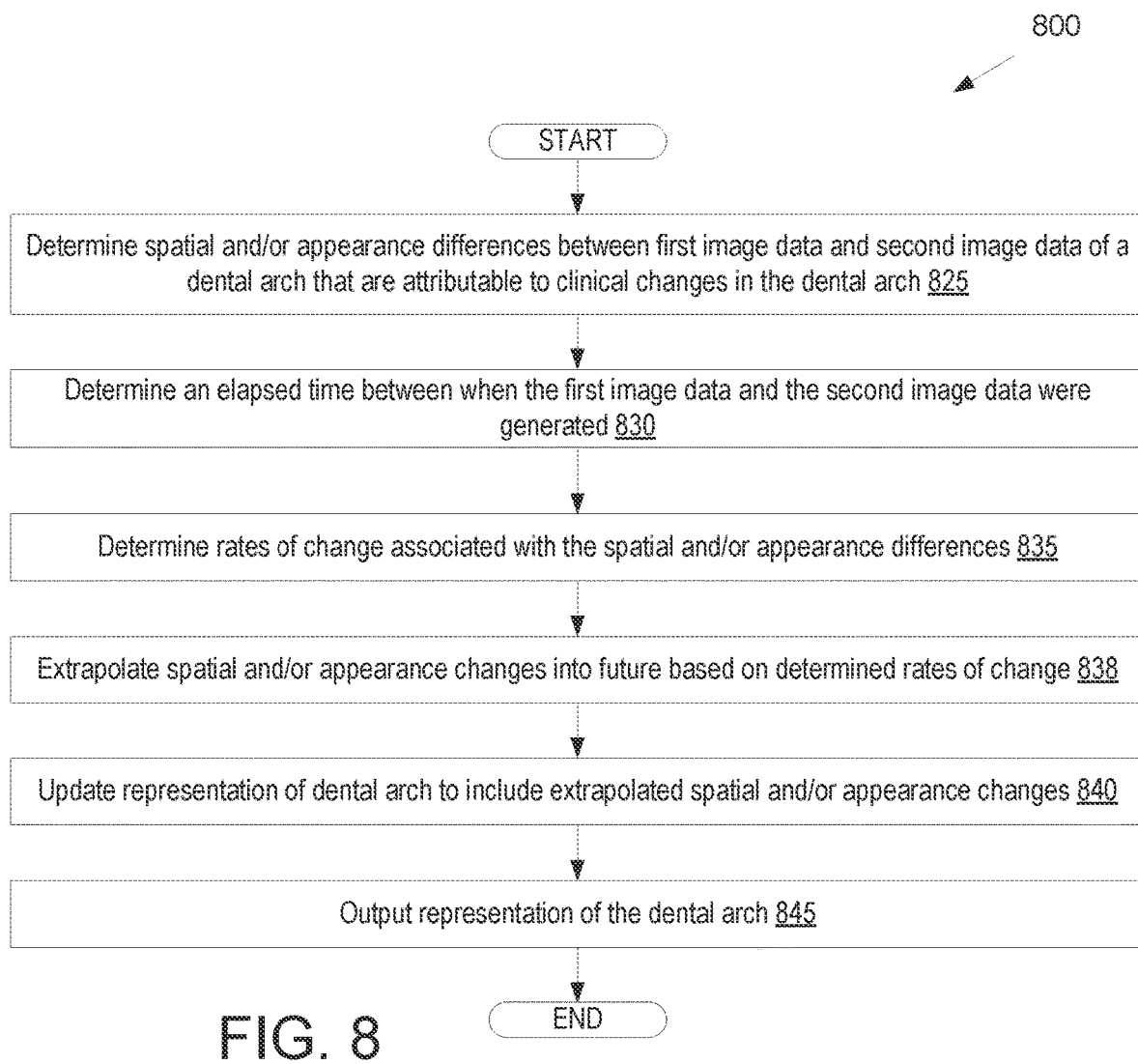
FIG. 8 illustrates a flow diagram for a method of generating a representation of a dental arch that accentuates changes that have occurred in the dental arch, in accordance with an embodiment.

FIG. 8 illustrates a flow diagram for a method 800 of generating a representation of a dental arch that accentuates changes that have occurred in the dental arch, in accordance with an embodiment. At block 825 of method 800, processing logic determines spatial and/or appearance differences between first image data (e.g., a first representation) and second image data (e.g., a second representation) of a dental arch that are attributable to clinical changes in the dental arch. After completion of method 200 and/or method 300, a point to point matching may have been determined (after applying smooth deformation to a test surface).

At block 830, processing logic determines an elapsed time between when the first image data and the second image data were generated. At block 835, processing logic determines rates of change associated with the spatial and/or appearance differences. At block 838, processing logic extrapolates the spatial and/or appearance differences into the future based on the determined rates of change. Processing logic may additionally or alternatively interpolate the differences between when the first and second image data was taken.

At block 840, processing logic updates a representation of the dental arch to include extrapolated or interpolated spatial and/or appearance changes. At block 845, processing logic outputs the representation of the dental arch showing the extrapolated or interpolated spatial and/or appearance changes.

Figure 9:
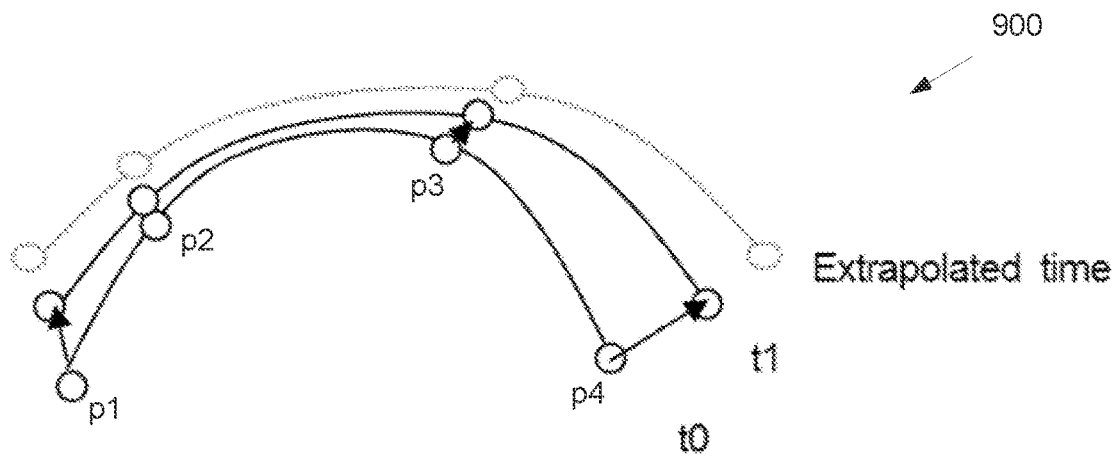
FIG. 9 illustrates extrapolated positions of a set of points on a dental arch.

FIG. 9 illustrates extrapolated positions of a set of points on a dental arch 900. As shown, each of points p1, p2, p3 and p4 have a first position at time t0 and a second position at a time t1. Extrapolation may be performed to determine a third position of the points p1, p2, p3 and p4 at an extrapolated time in the future.

A set of surfaces from past to future can be created to make an animated video of one or more clinical changes associated with the detected appearance and/or spatial differences in embodiments. The future portion of the video may also serve as an exaggeration of the clinical changes. Different frames of the video that show the differences between the two times may be generated by the interpolation, and additional frames of the video that show the differences after the second time may be generated by the extrapolation. The movement between frames may be controlled by a slider, showing the evolution of the clinical changes over time. If more than two measurements exist, interpolation between the multiple images may be used or a higher order extrapolation and/or interpolation may be used to increase an accuracy of the clinical changes over time. Techniques such as a parabolic function, splines, etc. may be used for this purpose.

Interpolating and extrapolating the trajectory of the appearance and spatial differences on a point by point basis can be prone to error and noise. Such error and noise may be reduced in embodiments by computing surface patches and computing trajectories of the surface patches. Processing logic may take small surface patches (e.g., 500×500 micron surface patches) containing many points and compute shared transformations between subsets of the surface patches. The transformation can be a non-rigid transformation, a rigid transformation, an affine transformation, and/or other transformation. The transformations can be restricted to be continuous to one another, or continuous and smooth (e.g., by comparing derivatives of the transformations between adjacent surface patches).

There are a number of different types of surface changes or movement that may be shown. Processing logic may use a different technique to visualize each type of surface change or movement. Tooth movement may be considered as a rigid body movement. To show tooth movement, a smooth non-rigid transformation (smooth deformation) may have been computed as set forth in methods 200 and 300. Additionally, tooth segmentation may be performed to identify individual teeth. Each tooth motion may then be estimated as an independent rigid body. The rigid body transformation for each tooth that has moved may be decomposed into translations (or position shifts) and rotations. To generate a trajectory of a tooth, processing logic may determine an interpolated transform between an initial reference position of the tooth and the final full motion of the tooth by rotating a partial angle and performing a partial translation. For an enhanced change, processing logic continues to apply the rotations and translations and project them to future times (e.g., using exponential mapping, matrix exponentiation, and so on).

Tooth grinding happens at specific portions of teeth (e.g., upper part of a tooth where contact occurs with teeth on an opposing jaw). To visualize tooth wear, processing logic may use a point to point comparison technique, but limit the change to the tooth shape to surface smoothness operations. Processing logic may interpolate to find intermediate tooth shapes and extrapolate to find future tooth shapes based on increasing the smoothness of the tooth.

Other techniques for interpolation and extrapolation may be used for visualizing other types of clinical changes such as tartar accumulation, sum swelling, gum recession, color change, and so on.

Changes that occur over time can be presented in various interfaces, including a side-to-side comparison, color mapping, an animation over time, a timeline slider, and so on. The timeline can include possible, predictive future changes and can have multiple paths based on treatment options selected by the dental practitioner.

After clinical changes are detected, processing logic may predict if clinical issues will occur in the near future as a result of the changes continuing. The extrapolation of the changes into the future may be applied to one or more thresholds to determine if clinical changes will be problematic for a patient. For example, a clinical change may not be problematic at present. However, extrapolation into the future may show that the clinical change will reach a critical point if it continues into the future. The critical point may be identified based on the one or more thresholds. For example, if tooth erosion will exceed a tooth erosion threshold at a future time, then that tooth erosion may be identified as problematic. This may assist a dental practitioner to take proactive measures like prescribing aligners, prescribing night guards, and so on.

In some embodiments, processing logic may track treatment milestones to track improvements or worsening conditions as a result of those milestones. Examples of milestones include crown delivery, orthodontic treatment, night guard delivery, tooth implant, and so on.

In some embodiments, the severity of detected spatial and appearance differences caused by clinical changes may be determined based on comparison to one or more thresholds. Such thresholds may be default values or selected by a dental practitioner. Such clinical changes may then be visualized based on the determined severity. For example, more severe clinical changes may be shown in a first color and less severe clinical changes may be shown in a second color. For example, hot colors such as red may show severe changes (e.g., tooth wear greater than 0.2 mm) and cold colors such as blue may show less severe changes (e.g., tooth wear of 0.05 mm or less). Other display options include adding bars that extend from a point of interest (e.g., a region of the dental arch associated with a detected clinical change), where the width of the bar is based on a severity of the clinical change. A user may be able to select the type of clinical change that is of interest, and only the selected type of clinical change may be shown for that selection.

Figure 10:
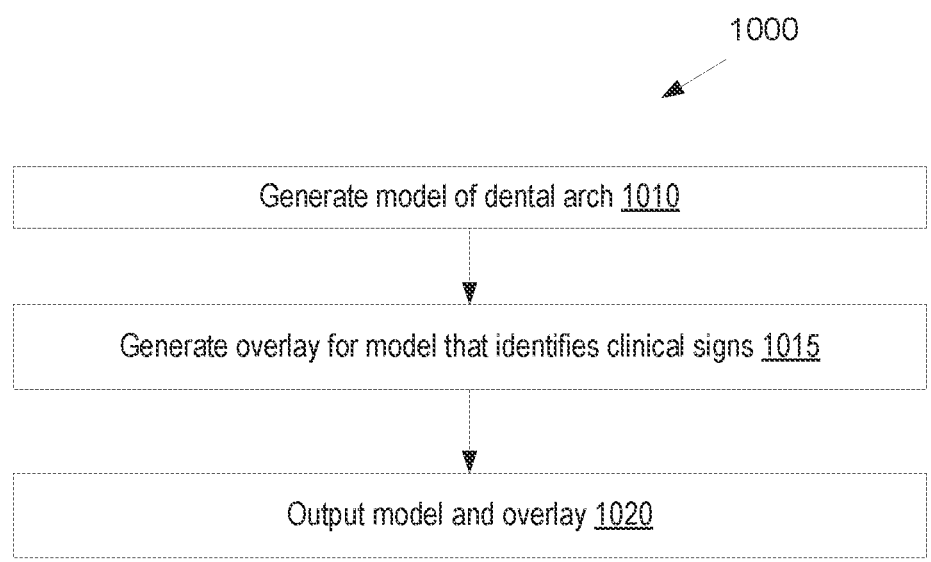
FIG. 10 illustrates a flow diagram for a method of generating a visual overlay for a virtual model of a dental arch, in accordance with an embodiment.

FIG. 10 illustrates a flow diagram for a method 1000 of generating a visual overlay for a virtual model of a dental arch, in accordance with an embodiment. The visual overlay may show compliance with an orthodontic treatment plan and deviation from the orthodontic treatment plan, in accordance with an embodiment. The visual overlay may additionally or alternatively show clinical changes to regions of a patient's dental arch. Method 1000 may be performed at the end of method 200. Method 1000 may also be performed in conjunction with method 300. At block 1010 of method 1000, processing logic generates a virtual model of the dental arch. The virtual model of the dental arch may be a generic model or may be a model tailored to a patient's specific dental arch (e.g., generated from an intraoral scan of the patient's dental arch). At block 1015, processing logic generates an overlay for the virtual model that identifies clinical signs that have been identified. The overlay may be a graphical overlay such as a color overlay that color codes teeth on the dental arch according to clinical signs associated with those teeth. At block 1020, processing logic outputs the virtual model and the overlay. Accordingly, the dental practitioner may easily determine what clinical changes have a been identified and where, and may at a glance determine how an orthodontic treatment plan is progressing.

Figure 15:
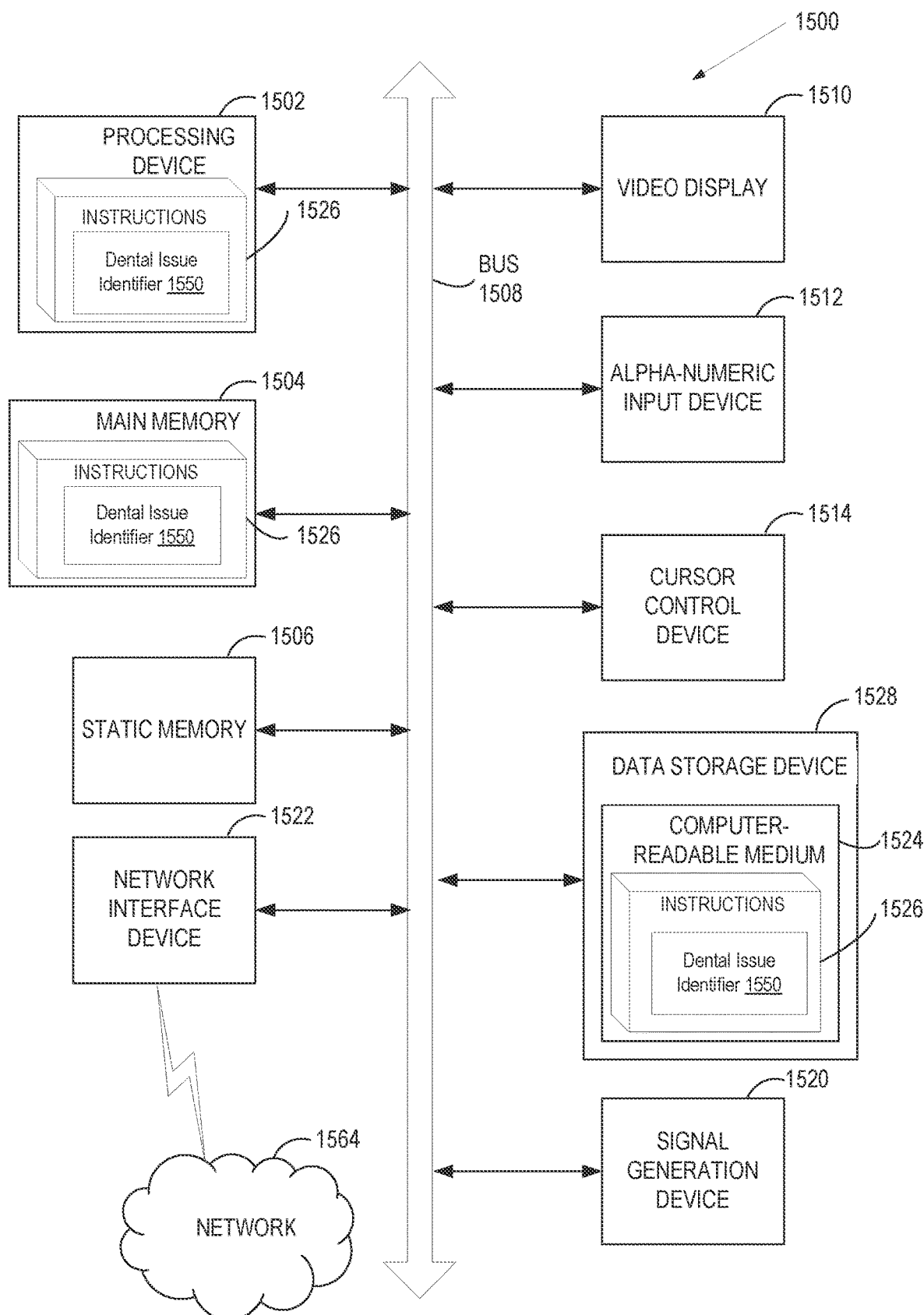
FIG. 15 illustrates a block diagram of an example computing device, in accordance with embodiments of the present invention.

FIG. 15 illustrates a diagrammatic representation of a machine in the example form of a computing device 1500 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 1500 corresponds to computing devices 155 of FIG. 1A.

The example computing device 1500 includes a processing device 1502, a main memory 1504 (e.g., read-only memory (ROM), flash memory, dynamic random access memory (DRAM) such as synchronous DRAM (SDRAM), etc.), a static memory 1506 (e.g., flash memory, static random access memory (SRAM), etc.), and a secondary memory (e.g., a data storage device 1528), which communicate with each other via a bus 1508.

Processing device 1502 represents one or more general-purpose processors such as a microprocessor, central processing unit, or the like. More particularly, the processing device 1502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1502 may also be one or more special-purpose processing devices such as an application specific integrated circuit (ASIC), a field programmable gate array (FPGA), a digital signal processor (DSP), network processor, or the like. Processing device 1502 is configured to execute the processing logic (instructions 1526) for performing operations and steps discussed herein.

The computing device 1500 may further include a network interface device 1522 for communicating with a network 1564. The computing device 1500 also may include a video display unit 1510 (e.g., a liquid crystal display (LCD) or a cathode ray tube (CRT)), an alphanumeric input device 1512 (e.g., a keyboard), a cursor control device 1514 (e.g., a mouse), and a signal generation device 1520 (e.g., a speaker).

The data storage device 1528 may include a machine-readable storage medium (or more specifically a non-transitory computer-readable storage medium) 1524 on which is stored one or more sets of instructions 1526 embodying any one or more of the methodologies or functions described herein, such as instructions for an AR processing module 1550. A non-transitory storage medium refers to a storage medium other than a carrier wave. The instructions 1526 may also reside, completely or at least partially, within the main memory 1504 and/or within the processing device 1502 during execution thereof by the computer device 1500, the main memory 1504 and the processing device 1502 also constituting computer-readable storage media.

The computer-readable storage medium 1524 may also be used to store a dental issue identifier 1550, which may correspond to the similarly named component of FIGS. 1A-1B. The computer readable storage medium 1524 may also store a software library containing methods for an dental issue identifier 1550. While the computer-readable storage medium 1524 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A non-transitory computer readable medium comprising instructions that, when executed by a processing device, cause the processing device to perform operations comprising:
   making a comparison between first image data of at least a portion of a dental arch and second image data of at least the portion of the dental arch;
   determining, by a processing device, a plurality of differences between a first representation of at least the portion of the dental arch in the first image data and a second representation of at least the portion of the dental arch in the second image data;
   determining, by the processing device, that a first difference of the plurality of differences is attributable to tooth movement;
   determining, by the processing device, that a second difference of the plurality of differences is attributable to tooth wear to one or more teeth on at least a portion of the dental arch; and
   generating, by the processing device, a third representation of at least the portion of the dental arch that is a modified version of the second representation, wherein a visual indication of the tooth wear is provided in the third representation.

2. The non-transitory computer readable medium of claim 1, wherein the plurality of differences comprise a plurality of spatial differences, wherein the first difference is a first spatial difference, and wherein the second difference is a second spatial difference.

3. The non-transitory computer readable medium of claim 1, the operations further comprising:
   providing a visual indication of a classification of the tooth wear in the third representation of at least the portion of the dental arch.

4. The non-transitory computer readable medium of claim 1, wherein determining that the first difference is attributable to tooth movement comprises:
   applying a detection rule associated with a tooth movement classification to the first difference; and
   determining that the first difference satisfies the detection rule.

5. The non-transitory computer readable medium of claim 1, wherein determining that the second difference is attributable to tooth wear comprises:
   applying a detection rule associated with a tooth wear classification to the second difference; and
   determining that the second difference satisfies the detection rule.

6. The non-transitory computer readable medium of claim 1, the operations further comprising:
   determining, by the processing device, that a third difference of the plurality of differences is attributable to scanner inaccuracy;
   wherein the third difference is removed in the third representation of at least the portion of the dental arch.

7. The non-transitory computer readable medium of claim 6, wherein determining that the third difference is attributable to scanner inaccuracy comprises:
   applying a low pass filter that identifies low frequency differences, wherein the third difference is a low frequency difference having a first value that is below a frequency threshold of the low pass filter and the first difference and second difference are higher frequency differences having values that are above the frequency threshold.

8. The non-transitory computer readable medium of claim 1, the operations further comprising:
   determining a magnitude of the second difference;
   comparing the magnitude of the second difference to one or more difference thresholds to determine a severity of the tooth wear; and
   providing the visual indication of the tooth wear based at least in part on the severity of the tooth wear.

9. The non-transitory computer readable medium of claim 1, the operations further comprising:
   extrapolating the second difference to a future time, wherein the tooth wear is more extensive after extrapolation, and wherein the third representation of at least the portion of the dental arch comprises a result of the extrapolation.

10. The non-transitory computer readable medium of claim 1, wherein the first representation comprises a first virtual three-dimensional (3D) model of the dental arch, the second representation comprises a second virtual 3D model of the dental arch, and the third representation comprises a third virtual 3D model of the dental arch.

11. The non-transitory computer readable medium of claim 1, wherein the first representation is generated based on an intraoral scan of the dental arch, and wherein the second representation is generated based at least in part on one or more two-dimensional images of the dental arch.

12. The non-transitory computer readable medium of claim 1, the operations further comprising:
   making a comparison of the tooth movement to a planned tooth movement;
   determining, based on the comparison of the tooth movement to the planned tooth movement, whether the tooth movement deviates from the planned tooth movement by more than a threshold amount; and
   generating a visual indicator that indicates whether the tooth movement deviates from the planned tooth movement by more than the threshold amount.

13. The non-transitory computer readable medium of claim 1, wherein:
   determining, by the processing device, that the first difference of the plurality of differences is attributable to tooth movement comprises determining that the first difference occurs at a first scale of a tooth size; and
   determining, by the processing device, that the second difference of the plurality of differences is attributable to tooth wear comprises determining that the second difference occurs at a second scale of a tooth tip.

14. A non-transitory computer readable medium comprising instructions that, when executed by a processing device, cause the processing device to perform operations comprising:

receiving first image data of at least a portion of a dental arch, wherein the first image data is based on an intraoral scan of the dental arch taken at a first time;

receiving second image data of at least the portion of the dental arch, wherein the second image data is based at least in part on one or more two-dimensional (2D) images of the dental arch taken at a second time that is later than the first time;

making a comparison between first image data and the second image data;

determining, by a processing device, a plurality of differences between a first representation of at least the portion of the dental arch in the first image data and a second representation of at least the portion of the dental arch in the second image data;

determining that one or more first differences of the plurality of differences are attributable to scanner inaccuracy;

determining that one or more second differences of the plurality of differences are attributable to a clinical change to at least the portion of the dental arch; and generating, by the processing device, a third representation of at least the portion of the dental arch that is a modified version of the second representation, wherein the one or more first differences of the plurality of differences are removed in the third representation.

15. The non-transitory computer readable medium of claim 14, wherein determining that the one or more first differences are attributable to scanner inaccuracy and that the one or more second differences are attributable to the clinical change to at least the portion of the dental arch comprises:

applying a low pass filter that identifies low frequency differences, wherein the one or more first differences are low frequency differences having one or more first values that are below a frequency threshold of the low pass filter and the one or more second differences are higher frequency differences having one or more second values that are above the frequency threshold.

16. The non-transitory computer readable medium of claim 14, the one or more 2D images having been generated by a camera.

17. The non-transitory computer readable medium of claim 14, wherein the first image data comprises a first three-dimensional (3D) model of at least the portion of the dental arch generated based on the intraoral scan of the dental arch, and wherein the second image data comprises a second 3D model of at least the portion of the dental arch generated based on the one or more 2D images of the dental arch.

18. A non-transitory computer readable medium comprising instructions that, when executed by a processing device, cause the processing device to perform operations comprising:

receiving first image data of at least a portion of a dental arch, wherein the first image data is based on an intraoral scan of the dental arch taken at a first time;

receiving second image data of at least the portion of the dental arch, wherein the second image data is based at least in part on one or more two-dimensional (2D) images of the dental arch taken at a second time that is later than the first time;

making a comparison between the first image data and the second image data;

determining, by a processing device, a plurality of differences between a first representation of at least the portion of the dental arch in the first image data and a second representation of at least the portion of the dental arch in the second image data;

determining, by the processing device, that a first difference of the plurality of differences is attributable to tooth movement;

determining, by the processing device, that a second difference of the plurality of differences is attributable to tooth wear to one or more teeth on at least a portion of the dental arch; and generating, by the processing device, a third representation of at least the portion of the dental arch that is a modified version of the second representation, wherein at least one of a) one or more first differences of the plurality of differences are removed in the third representation or b) visual indications of one or more second differences of the plurality of differences are provided in the third representation, the one or more second differences comprising the first difference and the second difference, wherein a visual indication of the tooth wear is provided in the third representation.

19. A non-transitory computer readable medium comprising instructions that, when executed by a processing device, cause the processing device to perform operations comprising:

receiving first image data of at least a portion of a dental arch, wherein the first image data is based on an intraoral scan of the dental arch taken at a first time;

receiving second image data of at least the portion of the dental arch, wherein the second image data is based at least in part on one or more two-dimensional (2D) images of the dental arch taken at a second time that is later than the first time;

making a comparison between first image data and the second image data;

determining, by a processing device, a plurality of differences between a first representation of at least the portion of the dental arch in the first image data and a second representation of at least the portion of the dental arch in the second image data;

determining a classification for a difference of the plurality of differences that is attributable to a clinical change; and generating, by the processing device, a third representation of at least the portion of the dental arch that is a modified version of the second representation, wherein at least one of a) one or more first differences of the plurality of differences are removed in the third representation or b) visual indications of one or more second differences of the plurality of differences are provided in the third representation, the one or more second differences comprising the difference that is attributable to clinical change, wherein a visual indication of the classification is provided in the third representation of at least the portion of the dental arch.

20. The non-transitory computer readable medium of claim 19, wherein the difference is a spatial difference, wherein the classification for the difference is a tooth movement classification, and wherein determining the tooth movement classification comprises:

applying a detection rule associated with the tooth movement classification to the difference; and determining that the difference satisfies the detection rule.

21. The non-transitory computer readable medium of claim 19, wherein the difference is a spatial difference, wherein the classification for the difference is a gum recession classification, and wherein determining the gum recession classification comprises:

applying a detection rule associated with the gum recession classification to the difference; and
determining that the difference satisfies the detection rule.

22. The non-transitory computer readable medium of claim 19, wherein the difference is a spatial difference, wherein the classification for the difference is a tooth wear classification, and wherein determining the tooth wear classification comprises:
applying a detection rule associated with the tooth wear classification to the difference; and
determining that the difference satisfies the detection rule.

23. The non-transitory computer readable medium of claim 19, wherein the difference is a spatial difference, wherein the classification for the difference is a gum swelling classification, and wherein determining the gum swelling classification comprises:
applying a detection rule associated with the gum swelling classification to the difference; and
determining that the difference satisfies the detection rule.

24. The non-transitory computer readable medium of claim 19, wherein the difference is a spatial difference in arch length between the first representation of at least the portion of the dental arch and the second representation of at least the portion of the dental arch.

25. The non-transitory computer readable medium of claim 19, the operations further comprising:
determining a magnitude of the difference;
comparing the magnitude of the difference to one or more difference thresholds to determine a severity of the clinical change; and
providing a visual indication based at least in part on the severity of the clinical change.

26. A non-transitory computer readable medium comprising instructions that, when executed by a processing device, cause the processing device to perform operations comprising:
receiving first image data of at least a portion of a dental arch, wherein the first image data is based on an intraoral scan of the dental arch taken at a first time;
receiving second image data of at least the portion of the dental arch, wherein the second image data is based at least in part on one or more two-dimensional (2D) images of the dental arch taken at a second time that is later than the first time;
making a comparison between first image data and the second image data;
determining, by a processing device, a plurality of differences between a first representation of at least the portion of the dental arch in the first image data and a second representation of at least the portion of the dental arch in the second image data, wherein the plurality of differences comprise a plurality of appearance differences, wherein an appearance difference comprises a difference in at least one of color, translucency, transparency, hue or intensity between a region in the first representation and a corresponding region in the second representation; and
generating, by the processing device, a third representation of at least the portion of the dental arch that is a modified version of the second representation, wherein at least one of a) one or more first differences of the plurality of differences are removed in the third representation or b) visual indications of one or more second differences of the plurality of differences are provided in the third representation.

27. A non-transitory computer readable medium comprising instructions that, when executed by a processing device, cause the processing device to perform operations comprising:
receiving first image data of at least a portion of a dental arch, wherein the first image data is based on an intraoral scan of the dental arch taken at a first time;
receiving second image data of at least the portion of the dental arch, wherein the second image data is based at least in part on one or more two-dimensional (2D) images of the dental arch taken at a second time that is later than the first time;
making a comparison between first image data and the second image data;
determining, by a processing device, a plurality of differences between a first representation of at least the portion of the dental arch in the first image data and a second representation of at least the portion of the dental arch in the second image data;
extrapolating a difference of the plurality of differences to a future time, wherein the difference is more extensive after extrapolation; and
generating, by the processing device, a third representation of at least the portion of the dental arch that is a modified version of the second representation, wherein at least one of a) one or more first differences of the plurality of differences are removed in the third representation or b) visual indications of one or more second differences of the plurality of differences are provided in the third representation, wherein the third representation of at least the portion of the dental arch comprises a result of the extrapolation.

28. A non-transitory computer readable medium comprising instructions that, when executed by a processing device, cause the processing device to perform operations comprising:
receiving first image data of at least a portion of a dental arch, wherein the first image data is based on an intraoral scan of the dental arch taken at a first time;
receiving second image data of at least the portion of the dental arch, wherein the second image data is based at least in part on one or more two-dimensional (2D) images of the dental arch taken at a second time that is later than the first time;
making a comparison between the first image data and the second image data;
determining, by a processing device, a plurality of differences between a first representation of at least the portion of the dental arch in the first image data and a second representation of at least the portion of the dental arch in the second image data, wherein at least one difference of the plurality of differences comprises an actual tooth movement for a tooth;
making a comparison of the actual tooth movement for the tooth to a planned tooth movement for the tooth;
determining, based on the comparison of the actual tooth movement for the tooth to a planned tooth movement for the tooth, whether the actual tooth movement deviates from the planned tooth movement by more than a threshold amount;
generating, by the processing device, a third representation of at least the portion of the dental arch that is a modified version of the second representation, wherein at least one of a) one or more first differences of the plurality of differences are removed in the third representation or b) visual indications of one or more second differences of the plurality of differences are provided in the third representation, the one or more second differences comprising the at least one difference; and generating a visual indicator that indicates whether the actual tooth movement deviates from the planned tooth movement by more than the threshold amount.

* * * * *